United States Patent [19]

Chabrecek et al.

[11] Patent Number: 5,527,925

[45] Date of Patent: Jun. 18, 1996

[54] FUNCTIONALIZED PHOTOINITIATORS, MACROMERS THEREOF, AND THE USE THEREOF

[75] Inventors: Peter Chabrecek, Basel; Dieter Lohmann, Münchenstein, both of Switzerland

[73] Assignee: Ciba-Geigy Corporation, Tarrytown, N.Y.

[21] Appl. No.: 265,597

[22] Filed: Jun. 24, 1994

[30] Foreign Application Priority Data

Jul. 2, 1993 [CH] Switzerland ............... 2006/93

[51] Int. Cl.$^6$ .................. C08F 2/50; C07C 249/00; C07C 251/00; C07D 317/32
[52] U.S. Cl. .................. 549/430; 560/330; 560/355; 560/358; 560/360; 523/106; 522/35; 522/904; 522/39; 522/40; 522/42
[58] Field of Search .................. 522/35, 39, 904, 522/40, 42; 560/330, 334, 355, 360, 358; 549/430; 523/106

[56] References Cited

U.S. PATENT DOCUMENTS

| 4,200,762 | 4/1980 | Schmidle | 528/75 |
| 4,224,454 | 9/1980 | McDowell et al. | 560/12 |

FOREIGN PATENT DOCUMENTS

| 12624/88 | 9/1988 | Australia . | |
| 281941 | 9/1988 | European Pat. Off. | C08F 2/50 |
| 63-57038 | 3/1988 | Japan . | |
| 63-53562 | 3/1988 | Japan . | |
| 1109086 | 5/1989 | Japan . | |

OTHER PUBLICATIONS

Chemical Abstract, #180747 Maslyuk, A. F, et al. 'Synthesis of oligurethanes capable of polymerization and properties of polyurethanes based on them', vol. 89, No. 22, 27 (Nov. 1978).

*Primary Examiner*—Susan W. Berman
*Attorney, Agent, or Firm*—Edward McC. Roberts; R. Scott Meece

[57] ABSTRACT

Compounds of formula I:

$$XCN-R_4-NHC(X)-Y-R_5-(Y_2)_n-\text{[aryl]}-C(O)-C(Y_1)_n-R_2, (Y_1)_n-R_1, (Y_1)_n-R_1, R$$

are disclosed. The compounds are photoinitiators which can be functionalized by means of ethylenic groups or can be bonded to H-active substances, in order, for example, to modify surfaces by means of photopolymerizable substances. The compounds are especially useful in the manufacture of contact lenses.

35 Claims, No Drawings

FUNCTIONALIZED PHOTOINITIATORS, MACROMERS THEREOF, AND THE USE THEREOF

The present invention relates to hydroxyl-containing acetophenones which have been functionalized by means of organic diisocyanates; to oligomers and polymers to which functionalized acetophenones of this type are bonded; to polymerizable photoinitiators; to ethylenically unsaturated acetophenones linked via a bifunctional diisocyanate linker; to the use of all these acetophenones as photoinitiators; to coated materials; and to the use of functionalized acetophenones for the modification of surfaces.

The compounds of the alkylphenone type or hydroxyalkylphenone type containing the structural unit of the formula (A)

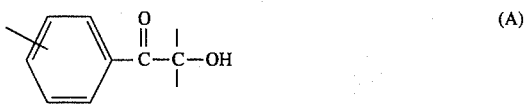

are excellent photoinitiators for radiation-induced polymerization of ethylenically unsaturated, monomeric, oligomeric or polymeric compounds. A particular disadvantage in many cases is found to be a discoloration (yellowing) of the polymers formed and the toxic properties of the resultant low-molecular-weight fragments, which can impair the use properties of the polymers prepared in this way. In order to avoid this disadvantage and other disadvantages of such monomeric photoinitiators, EP-A-0 281 941 proposes modifying photoinitiators on the phenyl ring in such a way that the photolysis products are strongly bonded in the resultant polymer association. Very generally, isocyanate groups are also mentioned as functional groups for this purpose, bonded to the phenyl ring via a spacer group, for example a linear alkylene group. However, the preparation of such compounds causes considerable synthetic problems, since the formation of diadducts cannot be avoided, and even predominates, in the reaction of linear diisocyanates with hydroxyl-containing compounds.

There is a demand for functional photoinitiators containing structural units of the formula (A) which are simple to prepare, can be obtained in high purity, are distinguished by high reactivity and a long shelf life and can be adducted onto suitable oligomers or polymers in order to prepare macromeric photoinitiators of high activity which are suitable for the modification of surfaces, in particular surfaces of plastics, by photoinduced graft polymerization, and can also be used for biocompatible materials, in particular in the biomedical sector, for example for contact lenses. It has been found that this object can be achieved if the introduction of isocyanate groups is carried out by reacting diisocyanates containing isocyanate groups of different reactivity with functional groups bonded to the phenyl ring in the formula (A), or reacting the hydroxyl group in the structural unit (A) with diisocyanates, thus suppressing, through high regioselectivity, the formation of isomers and other byproducts.

The invention relates to compounds of the formula I or Ia

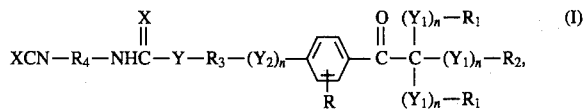

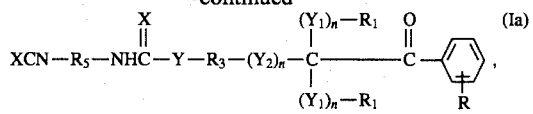

in which X is O; Y is O, NH or $NR_6$; $Y_1$ is O; $Y_2$ is $-O-$, $-O-(O)C-$, $-C(O)-O-$ or $-O-C(O)-O-$; the n indices, independently of one another, are 0 or 1; R is H, $C_1-C_{12}$alkyl, $C_1-C_{12}$alkoxy or $C_1-C_{12}$alkyl-NH—; the $R_1$ and $R_2$ radicals, independently of one another, are H, linear or branched $C_1-C_8$alkyl, $C_1-C_8$hydroxyalkyl or $C_6-C_{10}$aryl, or two groups $R_1-(Y_1)_n-$ together are $-(CH_2)_x-$, or the $R_1-(Y_1)_n-$ and $R_2-(Y_1)_n-$ groups together form a radical of the formula

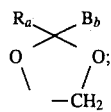

$R_3$ is a direct bond or linear or branched $C_1-C_8$alkylene, which is unsubstituted or substituted by —OH and/or is uninterrupted or interrupted by one or more $-O-$, $-O-C(O)-$ or $-O-C(O)-O-$ groups; $R_4$ is branched $C_3-C_{18}$alkylene, $C_6-C_{10}$arylene which is unsubstituted or substituted by $C_1-C_4$alkyl or $C_1-C_4$alkoxy, $C_7-C_{18}$aralkylene which is unsubstituted or substituted by $C_1-C_4$alkyl or $C_1-C_4$alkoxy, $C_3-C_8$cycloalkylene which is unsubstituted or substituted by $C_1-C_4$alkyl or $C_1-C_4$alkoxy, $C_3-C_8$cycloalkylene—$C_yH_{2y}-$ which is unsubstituted or substituted by $C_1-C_4$alkyl or $C_1-C_4$alkoxy, or $-C_yH_{2y}-$($C_3-C_8$cycloalkylene)—$C_yH_{2y}-$ which is unsubstituted or substituted by $C_1-C_4$alkyl or $C_1-C_4$alkoxy; each $R_5$, independently of the others, has the same meaning as $R_4$ or is linear $C_3-C_{18}$alkylene; $R_6$ is linear or branched $C_1-C_6$alkyl; x is an integer from 3 to 5; y is an integer from 1 to 6; $R_a$ and $R_b$, independently of one another, are H, $C_1-C_8$alkyl, $C_3-C_8$cycloalkyl, benzyl or phenyl; with the provisos that n in the $-(Y_1)_n-R_1$ groups is 0 if $R_2$ is H; that at most two $Y_1$ radicals in the $-(Y_1)_n-$ groups in the formula I are O and n in the other $-(Y_1)_n-$ groups is 0; that at most one $Y_1$ in the $-(Y_1)_n-$ groups in the formula Ia is O and n in the other $-(Y_1)_n-$ group is 0; and that n in the $-(Y_2)_n-$ group is 0 if $R_3$ is a direct bond.

In a preferred embodiment, Y is O.

Alkyl $R_6$ can be, for example, methyl, ethyl, n- or i-propyl, n-, i- or t-butyl, pentyl or hexyl. $R_6$ is preferably methyl.

Alkyl, alkoxy or alkyl-NH-R preferably contains 1 to 6, particularly preferably 1 to 4, carbon atoms. Some examples are methyl, ethyl, n- and i-propyl, n-, i- and t-butyl, pentyl, hexyl, octyl, decyl, dodecyl, methoxy, ethoxy, propoxy, butoxy and methyl-NH—. R is particularly preferably H.

Alkyl $R_1$ is preferably linear and preferably contains 1 to 4 carbon atoms. Some examples are methyl, ethyl, n- and i-propyl, n-, i- and t-butyl, pentyl, hexyl, heptyl and octyl. $R_1$ is particularly preferably methyl or ethyl. Aryl $R_1$ can be, for example, naphthyl, in particular phenyl. If both $R_1-(Y_1)_n-$ groups are $-(CH_2)_x-$, x is preferably 4, particularly preferably 5. Hydroxyalkyl $R_1$ is preferably linear and preferably contains 1 to 4 carbon atoms. Some examples are hydroxymethyl and 2-hydroxy-1-ethyl.

The same preferences apply to $R_2$ as for $R_1$. $R_2$ is particularly preferably H, methyl or ethyl.

$R_a$ and $R_b$ are preferably, independently of one another, H or $C_1-C_4$alkyl, for example methyl or ethyl.

In a preferred sub-group, $R_1$ is preferably ethyl, particularly preferably methyl, or both $R_1-(Y_1)_n-$ groups together are pentamethylene, n in the —(Y$_1$)$_n$—R$_2$ group is preferably 0, R$_2$ is preferably methyl, hydroxymethyl or H, and R is preferably H.

In another preferred embodiment, Y$_1$ in the —(Y$_1$)$_n$—R$_2$ group is O, n is 1 and R$_2$ is H. In this case, n in the R$_1$—(Y$_1$)$_n$— groups is in particular 0.

Alkylene R$_3$ preferably contains 1 to 6, particularly preferably 1 to 4, carbon atoms and the alkylene is preferably linear. Some examples are methylene, ethylene, 1,2- and 1,3-propylene, 1,2-, 1,3- and 1,4-butylene, pentylene, hexylene, heptylene and octylene. Preference is given to methylene, ethylene, 1,3-propylene and 1,4-butylene. R$_3$ is very particularly preferably ethylene or a direct bond, in which case n in the —(Y$_2$)$_n$— group is 0.

Hydroxy-substituted alkylene R$_3$ can in particular be, for example, 2-hydroxy-1,3-propylene or 2-hydroxy-1,3- or 1,4-butylene. Alkylene which is interrupted by —O— and is unsubstituted or substituted by —OH is, for example, —CH$_2$CH$_2$—O—CH$_2$CH$_2$—,     —CH$_2$CH$_2$—O—CH$_2$CH$_2$—O—CH$_2$CH$_2$—,  —CH$_2$CH$_2$—O—CH$_2$CH$_2$—O—CH$_2$CH$_2$—O—CH$_2$CH$_2$—,  [—CH(CH$_3$)CH$_2$—O—CH(CH$_3$)CH$_2$—],     —CH(CH$_3$)CH$_2$—O—CH$_2$CH$_2$—, —CH(C$_2$H$_5$)CH$_2$—O—CH$_2$CH$_2$—,  [—CH(C$_2$H$_5$)CH$_2$—O—CH(C$_2$H$_5$)CH$_2$—],     —CH$_2$CH$_2$CH$_2$CH$_2$—O—CH$_2$CH$_2$CH$_2$CH$_2$—   or   —CH$_2$CH(OH)CH$_2$—O—CH$_2$CH$_2$—. Alkylene which is interrupted by —O—C(O)— or —C(O)—O— is, for example, —CH$_2$CH$_2$—C(O)—O—CH$_2$— or —CH$_2$CH$_2$—O—C(O)—CH$_2$—. Alkylene which is interrupted by —O—C(O)—O— is, for example, —CH$_2$CH$_2$—O—C(O)—O—CH$_2$CH$_2$— or —CH$_2$CH$_2$—O—C(O)—O—CH$_2$—.

The C$_1$–C$_4$alkyl and C$_1$–C$_4$alkoxy substituents are preferably methyl, ethyl, methoxy or ethoxy.

Branched alkylene R$_4$ preferably contains 3 to 14, particularly preferably 4 to 10, carbon atoms. Examples of alkylene are 1,2-propylene, 2-methyl- and 2,2-dimethyl-1,3-propylene, 1,2-, 1,3- and 2,3-butylene, 2-methyl- and 2,3-dimethyl-1,4-butylene, 1,2-, 1,3- and 1,4-pentylene, 2-methyl- and 3-methyl- and 4-methyl- and 2,3-dimethyl- and 2,4-dimethyl and 3,4-dimethyl- and 2,3,4-trimethyl and 2,2,3-trimethyl-2,2,4-trimethyl- and 2,2,3,3-tetramethyl- and 2,2,3,4-tetramethyl-1,5-pentylene, 1,2-, 1,3-, 1,4- and 1,5-hexylene, 2-methyl- and 3-methyl and 4-methyl- and 2,2-dimethyl- and 3,3-dimethyl- and 2,3-dimethyl- and 2,4-dimethyl- and 3,4-dimethyl- and 2,2,3-trimethyl- and 2,2,4-trimethyl- and 2,2,5-trimethyl- and 2,3,4-trimethyl- and 2,2,4,5-tetramethyl-1,6-hexylene, 1,2-, 1,3-, 1,4-1,5 and 1,6-heptylene, 2-methyl- and 3-methyl- and 4-methyl- and 5-methyl- and 2,2-dimethyl- and 3,3-dimethyl- and 2,3-dimethyl- and 2,4-dimethyl- and 3,4-dimethyl- and 2,2,3-trimethyl- and 2,2,4-trimethyl- and 2,2,5-trimethyl- and 2,2,6-trimethyl- and 2,3,4-trimethyl- and 2,4,5-trimethyl- and 2,4,6-trimethyl- and 2,2,4,5-tetramethyl-1,7-heptylene, 1,2-, 1,3-, 1,4- 1,5-,1,6- and 1,7-octylene, 2-methyl- and 3-methyl- and 4-methyl- and 5-methyl- and 6-methyl- and 7-methyl- and 2,2-dimethyl- and 3,3-dimethyl- and 2,3-dimethyl- and 2,4-dimethyl- and 3,4-dimethyl- and 2,6-dimethyl- and 2,7-dimethyl- and 2,2,4-trimethyl- and 2,2,5-trimethyl- and 2,2,6-trimethyl- and 2,2,5,6-tetramethyl-1,8-octylene, 1,2-, 1,3-, 1,4-1,5-1,6-, 1,7- and 1,8-nonylene, 2-methyl- and 3-methyl- and 4-methyl- and 5 -methyl- and 6-methyl- and 7-methyl- and 8-methyl and 2,2-dimethyl- and 3,3-dimethyl- and 2,3-dimethyl- and 2,4-dimethyl- and 3,4-dimethyl- and 2,6-dimethyl- and 2,7-dimethyl- and 2,8-dimethyl- and 2,2,4-trimethyl- and 2,2,5-trimethyl- and 2,2,6-trimethyl- and 2,2,7-trimethyl- and 2,2,8-trimethyl- nonylene, 1,2-, 1,3-, 1,4-1,5- 1,6-, 1,7-, 1,8- and 1,9-decylene, 2-methyl- and 3-methyl- and 4-methyl- and 5-methyl- and 6-methyl- and 7-methyl- and 8-methyl- and 9-methyl- and 2,2-dimethyl- and 3,3-dimethyl- and 2,3-dimethyl- and 2,4-dimethyl- and 3,4-dimethyl- and 2,6-dimethyl- and 2,7-dimethyl-, 2,8-dimethyl- and 2,9-dimethyl-1,10-decylene, 1,2-, 1,3-, 1,4-1,5-1,6-, 1,7-, 1,8-, 1,9- and 1,10-undecylene, 2-methyl- and 3-methyl- and 4-methyl- and 5-methyl- and 6-methyl- and 7-methyl- and 8-methyl- and 9-methyl- and 10-methyl-1,11-undecylene, 1,4-1,5-1,6-, 1,7-, 1,8-, 1,9-, 1,10- and 1,11-dodecylene.

Some preferred branched alkylene radicals are 2,2-dimethyl-1,4-butylene, 2,2-dimethyl-1,5-pentylene, 2,2,3- and 2,2,4-trimethyl-1,5-pentylene, 2,2-dimethyl-1,6-hexylene, 2,2,3- and 2,2,4- and 2,2,5-trimethyl-1,6-hexylene, 2,2-dimethyl-1,7-heptylene, 2,2,3- and 2,2,4- and 2,2,5- and 2,2,6-trimethyl-1,7-heptylene, 2,2-dimethyl-1,8-octylene, 2,2,3- and 2,2,4- and 2,2,5- and 2,2,6- and 2,2,7-trimethyl-1,8-octylene.

Arylene R$_4$ is preferably naphthylene, particularly preferably phenylene. Any substituents on the arylene are preferably in the and tho-position to an isocyanate group. Examples of substituted arylene are 1-methyl-2,4-phenylene, 1,5-dimethyl-2,4-phenylene, 1-methoxy-2,4-phenylene and 1-methyl-2,7-naphthylene.

Aralkylene R$_4$ is preferably naphthylalkylene, particularly preferably phenylalkylene. The alkylene group in the aralkylene preferably contains 1 to 12, particularly preferably 1 to 6, especially preferably 1 to 4, carbon atoms. The alkylene group in the aralkylene is very particularly preferably methylene or ethylene. Some examples are 1,3- and 1,4-benzylene, naphth-2-yl-7-methylene, 6-methyl-1,3- and 1,4-benzylene, and 6-methoxy-1,3- and 1,4-benzylene.

Cycloalkylene R$_4$ is preferably C$_5$- and C$_6$cycloalkylene, which is unsubstituted and substituted by methyl. Some examples are 1,3-cyclobutylene, 1,3-cyclopentylene, 1,3- and 1,4-cyclohexylene, 1,3- and 1,4-cycloheptylene, 1,3- and 1,4- and 1,5-cyclooctylene, 4-methyl-1,3-cyclopentylene, 4-methyl-1,3-cyclohexylene, 4,4-dimethyl-1,3-cyclohexylene, 3-methyl- and 3,3-dimethyl-1,4-cyclohexylene, 3,5-dimethyl-1,3-cyclohexylene and 2,4-dimethyl-1,4-cyclohexylene.

Cycloalkylene-C$_y$H$_{2y}$—R$_4$ is preferably cyclopentylene-C$_y$H$_{2y}$—, particularly preferably cyclohexylene-C$_y$H$_{2y}$—, which is unsubstituted or substituted, preferably by 1 to 3 C$_1$–C$_4$alkyl radicals, particularly preferably by methyl. In the —C$_y$H$_{2y}$— group, y is preferably an integer from 1 to 4. The —C$_y$H$_{2y}$— group is more preferably ethylene and particularly preferably methylene. Some examples are cyclopent-1-yl-3-methylene, 3-methylcyclopent-1-yl-3-methylene, 3,4-dimethylcyclopent-1-yl-3-methylene, 3,4,4-trimethylcyclopent-1-yl-3-methylene, cyclohex-1-yl-3- and -4-methylene, 3- and 4- and 5-methylcyclohex-1-yl-3- and -4-methylene, and 3,4- and 3,5-dimethylcyclohex-1-yl-3- and -4-methylene, 3,4,5- and 3,4,4- and 3,5,5-trimethylcyclohex-1-yl-3- and -4-methylene.

—C$_y$H$_{2y}$-cycloalkylene-C$_y$H$_{2y}$—R$_4$ is preferably —C$_y$H$_{2y}$-cyclopentylene-C$_y$H$_{2y}$—, particularly preferably —C$_y$H$_{2y}$-cyclohexylene-C$_y$H$_{2y}$—, which is unsubstituted or substituted, preferably by 1 to 3 C$_1$–C$_4$alkyl radicals, particularly preferably by methyl. In the —C$_y$H$_{2y}$— group, y is preferably an integer from 1 to 4. The —C$_y$H$_{2y}$— group is more preferably ethylene and particularly preferably methylene. Some examples are cyclopentane-1,3-dimethylene, 3-methylcyclopentane-1,3-dimethylene, 3,4-dimethylcyclopentane-1,3-dimethylene, 3,4,4-trimethylcyclopentane-1,3-dimethylene, cyclohexane-1,3- and -1,4-dimethylene, 3- and 4- and 5-methylcyclohexane-1,3- and -1,4-dimethylene, 3,4- and 3,5-dimethylcyclohexane-1,3- and -1,4-dimethylene, 3,4,5- and 3,4,4- and 3,5,5-trimethylcyclohexane-1,3- and -1,4-dimethylene.

If $R_5$ has the same meaning as $R_4$, the preferences given above for $R_4$ also apply. Linear alkylene $R_5$ preferably contains 3 to 12, particularly preferably 3 to 8, carbon atoms. Some examples of linear alkylene are 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,14-tetradecylene and 1,18-octadecylene.

A preferred sub-group of compounds of the formulae I and Ia comprises those in which n in the $R_1$—$(Y_1)_n$— groups is O, X, Y, $Y_2$ and $Y_1$ in the $R_2$—$(Y_1)_n$— group are each O, n in the $R_2$—$(Y_1)_n$— group is 0 or 1, $R_1$ is $C_1$–$C_4$alkyl or phenyl, or the $R_1$—$(Y_1)_n$— groups together are tetramethylene or pentamethylene, $R_2$ is $C_1$–$C_4$alkyl or H, R is hydrogen, n in the —$(Y_2)_n$— group is 0 or 1, $R_3$ is linear or branched $C_2$–$C_4$alkylene or a direct bond, in which case n in the —$(Y_2)_n$— group is 0, $R_4$ is branched $C_5$–$C_{10}$alkylene, phenylene or phenylene which is substituted by 1 to 3 methyl groups, benzylene or benzylene which is substituted by 1 to 3 methyl groups, cyclohexylene or cyclohexylene which is substituted by 1 to 3 methyl groups, cyclohexyl-$C_yH_{2y}$— or —$C_yH_{2y}$-cyclohexyl-$C_yH_{2y}$— or cyclohexyl-$C_yH_{2y}$— or —$C_yH_{2y}$-cyclohexyl-$C_yH_{2y}$—, each of which is substituted by 1 to 3 methyl groups, $R_5$ is as defined for $R_4$ or is linear $C_3$–$C_{10}$alkylene, and y is 1 or 2.

A particularly preferred sub-group of compounds of the formulae I and Ia comprises those in which n in the $R_1$—$(Y_1)_n$ and —$(Y_2)_n$— groups is O, X, Y, $Y_2$ and $Y_1$ in the $R_2$—$(Y_1)_n$— group are each O, n in the $R_2$—$(Y_1)_n$— group is 0 or 1, $R_1$ is methyl or phenyl or the $R_1$—$(Y_1)_n$— groups together are pentamethylene, $R_2$ is methyl or H, R is hydrogen, n in the —$(Y_2)$—$_n$ group is 1 and $R_3$ is ethylene, or n in the —$(Y_2)_n$— group is 0 and $R_3$ is a direct bond, $R_4$ is branched $C_6$–$C_{10}$alkylene, phenylene or phenylene which is substituted by 1 to 3 methyl groups, benzylene or benzylene which is substituted by 1 to 3 methyl groups, cyclohexylene or cyclohexylene which is substituted by 1 to 3 methyl groups, cyclohexyl-$CH_2$— or cyclohexyl-$CH_2$— which is substituted by 1 to 3 methyl groups, and $R_5$ is as defined for $R_4$ or is linear $C_5$–$C_{10}$alkylene.

The $R_4$ and $R_5$ groups are in particular those which reduce the reactivity of the XCN group, which is essentially achieved by steric hindrance on at least one adjacent carbon atom. $R_4$ and $R_5$ are therefore preferably alkylene which is branched in the α- or in particular the β-position to the XCN group, or cyclic hydrocarbons which are substituted in at least one α-position as defined.

Some examples of particularly preferred compounds are

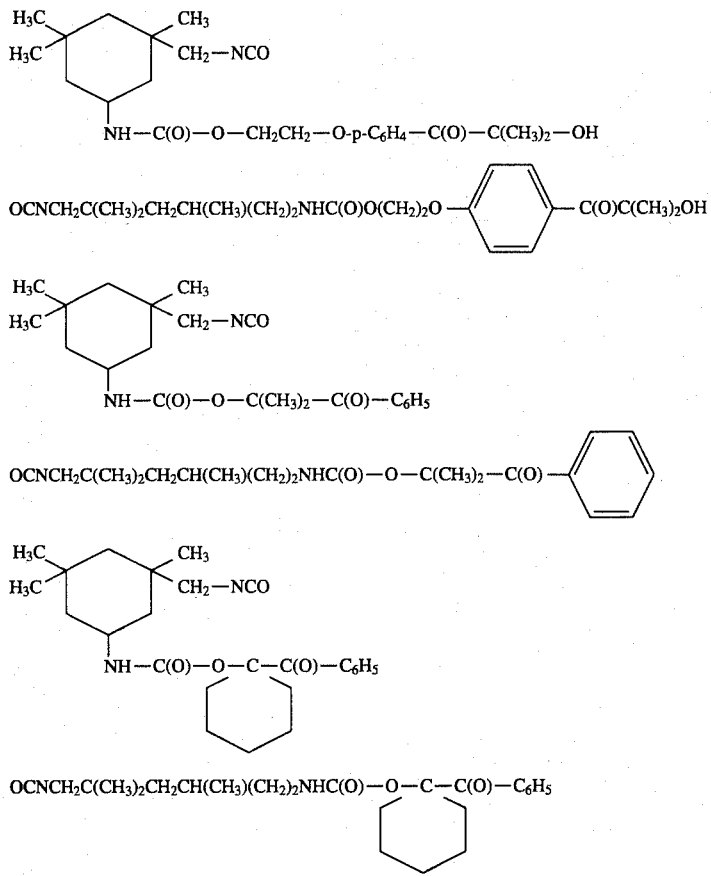

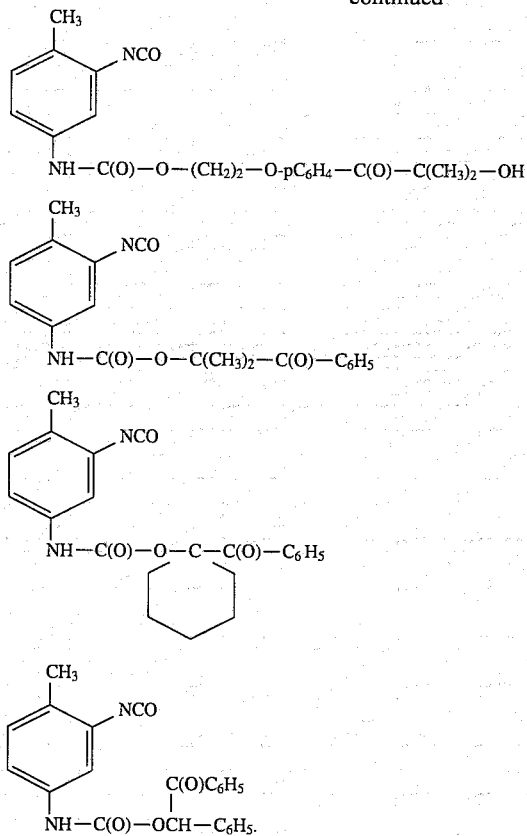

The compounds of the formulae I and Ia can be prepared in a manner known per se by reacting diisocyanates with the corresponding H-acidic photoinitiators. The compounds are obtained in high yields and purities, even if the photoinitiator simultaneously contains two H-acidic groups of different reactivity, for example 2 OH groups. It is particularly advantageous to use diisocyanates containing isocyanate groups of different reactivity, since this allows the formation of isomers and diadducts to be substantially suppressed. The different reactivity can be achieved, for example, as described above, by steric hindrance. The different reactivity can also be achieved by blocking an isocyanate group in the diisocyanate, for example by means of carboxylic acids or hydroxylamine.

The invention furthermore relates to a process for the preparation of the compounds of the formulae I and Ia, which comprises reacting a compound of the formula II or IIa

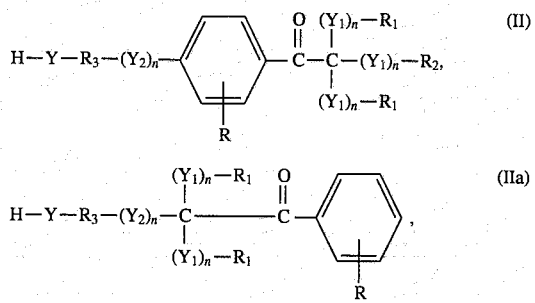

in which Y, $Y_1$, $Y_2$, R, $R_1$, $R_2$, $R_3$ and n are as defined above, with a diisocyanate of the formula III or IIIa $$XCN-R_4-NCX \qquad (III),$$

$$XCN-R_5-NCX \qquad (IIIa),$$

in which $R_4$, $R_5$ and X are as defined above, or an unblocked or monoblocked diisocyanate of this type, in an inert organic solvent, in particular at a temperature of up to 40° C., preferably at room temperature.

Blocking agents are known from urethane chemistry. They can be, for example, phenols (cresol or xylenol), lactams (ε-caprolactam), oximes (acetoxime or benzophenone oxime), H-active methylene compounds (diethyl malonate or ethyl acetoacetate), pyrazoles or benzotriazoles. Blocking agents are described, for example, by Z. W. Wicks, Jr. in Progress in Organic Coatings, 9 (1981), pages 3–28.

The compounds of the formulae II and IIa are known photoinitiators of the hydroxyalkylphenone type and are described in the literature [see, for example, H. F. Gruber, Prog. Polym. Sci, Vol. 17, pages 953 to 1044 (1992), Pergamon Press Ltd.]. The isocyanates are compounds which are well known from polyurethane chemistry.

Suitable inert solvents are aprotic, preferably polar solvents, for example hydrocarbons (petroleum ether, methylcyclohexane, benzene, toluene and xylene), halogenated hydrocarbons (chloroform, methylene chloride, trichloroethane, tetrachloroethane and chlorobenzene), ethers (diethyl ether, dibutyl ether, ethylene glycol dimethyl ether, diethylene glycol dimethyl ether, tetrahydrofuran and dioxane), ketones (acetone, dibutyl ketone and methyl isobutyl ketone), carboxylic esters and lactones (ethyl acetate, butyrolactone and valerolactone), alkylated carboxamides (N,N-dimethylacetamide and N-methylpyrrolidone), nitriles (acetonitrile), sulfones and sulfoxides (dimethyl sulfoxide and tetramethylene sulfone). Preference is given to polar solvents.

The reactants are advantageously employed in equimolar mounts. The reaction temperature can be, for example, from 0° to 200° C. If catalysts are used, the temperatures can expediently be in the range from 0° to 50° C., preferably at room temperature. Examples of suitable catalysts are metal salts, such as alkali metal salts of carboxylic acids, tertiary amines, for example ($C_1$–$C_6$alkyl)$_3$N(triethylamine and tri-n-butylamine), N-methylpyrrolidine, N-methylmorpholine, N,N-dimethylpiperidine, pyridine and 1,4-diazabicyclooctane. Tin salts, especially alkyl tin salts of carboxylic acids, for example dibutyltin dilaurate and tin dioctanoate, have proven particularly effective. If the compounds of the formulae II and IIa contain at least two hydroxyl groups, the reaction is expediently carded out at room temperature for selectivity reasons.

The compounds prepared are isolated and purified by known methods, for example by extraction, crystallization, recrystallization or chromatography. The compounds are obtained in high yields and purities. The yields in non-optimized processes can be greater than 85% of theory.

The compounds of the formulae I and Ia are highly suitable as photoinitiators for ethylenically unsaturated, free-radical-polymerizable compounds, in particular those which additionally contain H-active groups, for example OH—, —COOH, —CONH— or NH—groups. In this case, the photoinitiators are substantially covalently bonded to the polymers formed via the isocyanate group and the photochemical decomposition products (free radical initiators or chain terminators) and effectively prevent any associated impairment of the use properties. The invention furthermore relates to the use of the compounds of the formulae I and Ia as photoinitiators for ethylenically unsaturated, free-radical-polymerizable compounds, in particular those additionally containing H-active groups.

The compounds of the formulae I and Ia are also highly suitable for the preparation of oligomeric or polymeric photoinitiators by reaction with functional oligomers or polymers containing active H atoms, for example OH or NH groups. These macromeric photoinitiators are distinguished by good compatibility and high effectiveness, the photochemical decomposition products, as already stated, being covalently bonded in the polymers formed, for example as chain initiators or terminators, so that a long service life is ensured. A further advantage which should be mentioned is the particular structure of the photopolymers, since the polymer chains grow on the macromeric photoinitiator, giving further advantageous use properties. Thus, the properties desired can be established in a targeted way in the photopolymer through the choice of oligomers or polymers.

The invention furthermore relates to oligomers and polymers containing H-active groups —OH and/or —NH— bonded to the oligomer or polymer backbone, if desired via a bridge group, or containing H-active —NH— groups bonded in the oligomer or polymer backbone, some or all of whose H atoms have been substituted by radicals of the formulae IV and/or IVa in which R, $R_1$, $R_2$, $R_3$, $R_4$, $R_5$, X, Y, $Y_1$, $Y_2$ and n are as defined above, bonded to the oligomer or polymer backbone.

The H-active groups are principally —COOH, —OH or —NH— groups.

The oligomers can have a mean molecular weight of from 300 to 10 000 daltons and preferably contain at least 3, more preferably from 3 to 50, particularly preferably from 5 to 20, structural units. The distinction between oligomers and polymers is, as is known, fluid and cannot be defined precisely. The polymers can contain from 50 to 10 000, more preferably from 50 to 5000, structural units and have a mean molecular weight of from 10 000 to 1 000 000, preferably from 10 000 to 5 000 000. The oligomers and polymers can also contain up to 95 mol %, more preferably from 5 to 90 mol %, of comonomeric structural units without H-active groups, based on the polymer.

The oligomers and polymers containing H-active groups can be natural or synthetic oligomers or polymers.

Examples of natural oligomers and polymers are oligosaccharides and polysaccharides and derivatives thereof, proteins, glycoproteins, enzymes and growth factors. Some examples are cyclodextrins, starch, hyaluronic acid, deacetylated hyaluronic acid, chitosan, trehalose, cellobiose, maltotriose, maltohexaose, chitohexaose, agarose, chitin 50, amylose, glucans, heparin, xylan, pectin, galactan, glycosaminoglycans, dextran, aminated dextran, cellulose, hydroxyalkylcelluloses, carboxyalkylcelluloses, heparin, fucoidan, chondroitin sulfate, sulfated polysaccharides, mucopolysaccharides, gelatin, zein, collagen, albumin, globulin, bilirubin, ovalbumin, keratin, fibronectin and vitronectin, pepsin, trypsin and lysozymes.

The synthetic oligomers and polymers can be substances containing the —COOH, —OH, —$NH_2$ or —$NHR_7$ groups, where $R_7$ is $C_1$–$C_6$alkyl. They can be, for example, hydrolysed polymers of vinyl esters or ethers (polyvinyl alcohol), hydroxylated polydiolefins, for example polybutadiene, polyisoprene or chloroprene; polyacrylic acid, polymethacrylic acid and polyacrylates, polymethacrylates, polyacrylamides and polymethacrylamides containing hydroxyalkyl or aminoalkyl radicals in the ester group or amide group; polysiloxanes containing hydroxyalkyl or aminoalkyl groups; polyethers made from epoxides or glycidyl compounds and diols; polyvinylphenols or copolymers of vinylphenol and olefinic comonomers; and copolymers of at least one monomer from the group consisting of vinyl alcohol, vinylpyrrolidone, acrylic acid, methacrylic acid or hydroxyalkyl- or aminoalkyl-containing acrylates, methacrylates or acrylamide or methacrylamide, or hydroxylated diolefins with ethylenically unsaturated comonomers, for example acrylonitrile, olefins, diolefins, vinyl chloride, vinylidene chloride, vinyl fluoride, vinylidene fluoride, styrene, α-methylstyrene, vinyl ethers and vinyl esters; and polyoxaalkylenes containing terminal OH or aminoalkoxy groups.

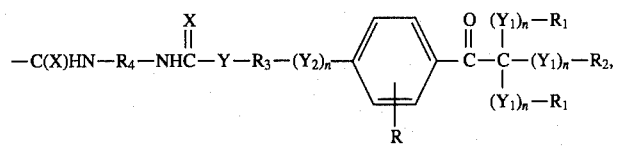

(IV)

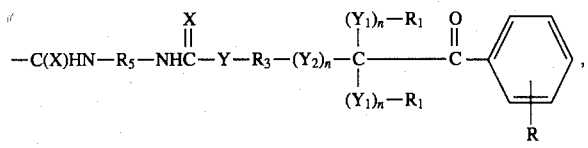

(IVa)

Examples of preferred oligomers and polymers are cyclodextrins containing a total of 6 to 8 glucose structural units forming a ring, and hydroxyalkyl and aminoalkyl derivatives and glucose- and maltose-substituted derivatives, of which at least one structural unit conforms to the formula XVI

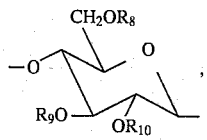
(XVI)

in which $R_8$, $R_9$ and $R_{10}$, independently of one another, are H, $C_1$–$C_4$alkyl, in particular methyl, $C_2$–$C_6$acyl, in particular acetyl, $C_1$–$C_4$hydroxyalkyl, in particular hydroxymethyl or 2-hydroxy-1-ethyl, $C_2$–$C_{10}$aminoalkyl and in particular $C_2$–$C_4$aminoalkyl, for example 2-amino-1-ethyl, 3-aminopropyl or 4-amino-1-butyl, and at least one of the radicals $R_8$, $R_9$ and $R_{10}$ is a radical of the formulae V and/or Va

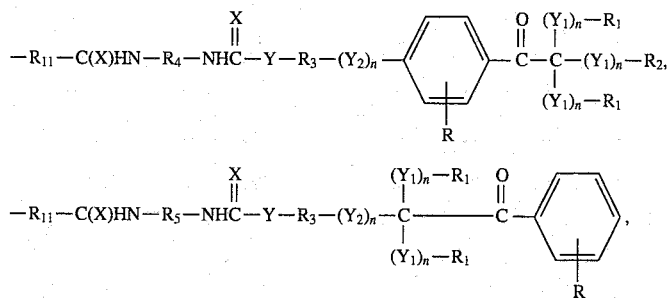

in which R, $R_1$, $R_2$, $R_3$, $R_4$, $R_5$, X, Y, $Y_1$, $Y_2$ and n are as defined above, and $R_{11}$ is a direct bond, —($C_1$–$C_4$alkylene-O)— or —($C_2$–$C_{10}$alkylene-NH)—.

In a preferred embodiment, from at least half the glucose units to all 6 to 8 glucose units contain at least one radical of the formula V or Va. The abovementioned preferences apply for R, $R_1$, $R_2$, $R_3$, $R_4$, $R_5$, X, Y, $Y_1$, $Y_2$ and n. $R_{11}$ preferably a direct bond, —$CH_2$—O—, —$CH_2CH_2$—O—, —$CH_2CH_2$—NH— or —$CH_2CH_2CH_2$—NH—.

Examples of other preferred oligomers and polymers are oligo- and polysiloxanes containing, in the alkyl terminal groups or side chains, OH or $NH_2$ groups whose H atoms have been substituted by a photoinitiator according to the invention. These can be random or block oligomers or block polymers. More preferred oligomers and polymers are those which contain a) from 5 to 100 mol % of structural units of the formula VI

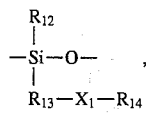
(VI)

and b) from 95 to 0 mol % of structural units of the formula VIa

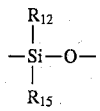
(VIa)

based on the oligomer or polymer, where $R_{12}$ is unsubstituted or partly or fully F-substituted $C_1$–$C_4$alkyl, vinyl, allyl or phenyl, preferably methyl or trifluoromethyl, $R_{13}$ is $C_2$–$C_6$alkylene, preferably 1,3-propylene, $R_{15}$ is as defined for $R_{12}$ or is —$R_{13}$—$X_1$—H or —$R_{13}$—$X_1$—$R_{16}$—H, $X_1$ is —O— or —NH—, and $R_{14}$ is a radical of the formulae VII or VIIa,

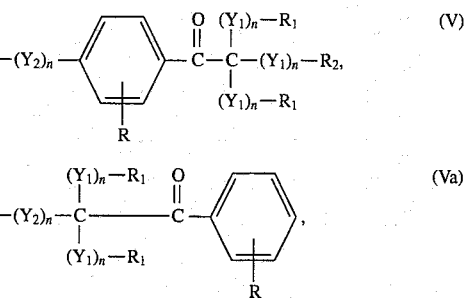

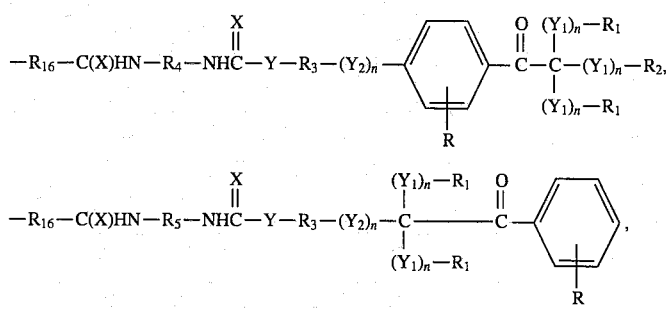

in which R, $R_1$, $R_2$, $R_3$, $R_4$, $R_5$, X, Y, $Y_1$, $Y_2$ and n are as defined above, and $R_{16}$ is a direct bond or a —C(O)—(CHOH)$_r$—$CH_2$—O— group, in which r is 0 or an integer from 1 to 4. The abovementioned preferences apply for R, $R_1$, $R_2$, $R_3$, $R_4$, $R_5$, X, Y, $Y_1$, $Y_2$ and n. $X_1$ is preferably —NH—.

Other preferred oligomeric or polymeric siloxanes are those of the formula VIII

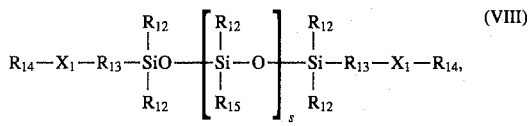

where $R_{12}$ is unsubstituted or partly or fully F-substituted $C_1$–$C_4$alkyl, vinyl, allyl or phenyl, preferably methyl or trifluoromethyl, $R_{13}$ is $C_2$–$C_6$alkylene, preferably 1,3-propylene, $R_{15}$ is as defined for $R_{12}$ or is —$R_{13}$—$X_1$—H or —$R_{13}$—$X_1$—$R_{16}$—H, $X_1$ is —O— or —NH—, and $R_{14}$ is a radical of the formulae VII or VIIa,

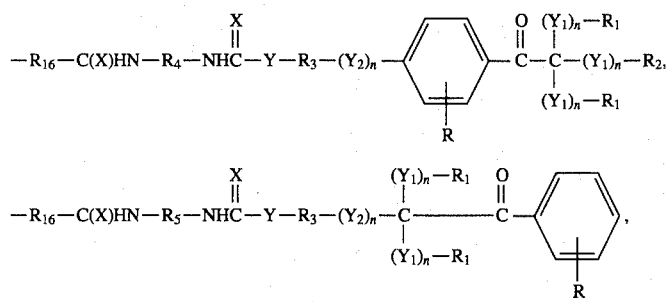

in which R, $R_1$, $R_2$, $R_3$, $R_4$, $R_5$, X, Y, $Y_1$, $Y_2$ and n are as defined above, and $R_{16}$ is a direct bond or a —C(O)—(CHOH)$_r$—CH$_2$—O— group, in which r is O or an integer from 1 to 4. The abovementioned preferences apply for R, $R_1$, $R_2$, $R_3$, $R_4$, $R_5$, X, Y, $Y_1$, $Y_2$ and n. $X_1$ is preferably —NH—.

Other preferred oligomers and polymers are those based on oligo- and polyvinyl alcohol in which some or all of the H atoms in the OH groups have been substituted by a radical of the formula V or Va. These can be homopolymers containing —CH$_2$CH(OH)— structural units or copolymers containing other univalent or divalent structural units of olefins.

More preferred are oligomers and polymers which contain a) from 5 to 100 mol % of structural units of the formula IX

and b) from 95 to 0 mol % of structural units of the formula X

in which $R_{17}$ is a radical of the formula V or Va

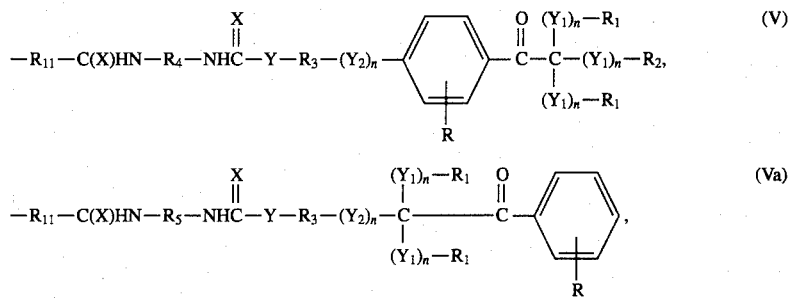

in which R, $R_1$, $R_2$, $R_3$, $R_4$, $R_5$, X, Y, $Y_1$, $Y_2$ and n are as defined above, and $R_{11}$ is a direct bond, —($C_1$–$C_4$alkylene-O)— or —($C_2$–$C_{10}$alkylene-NH)—; $R_{18}$ is H, $C_1$–$C_6$alkyl, —COOR$_{21}$ or —COO$^\ominus$, $R_{19}$ is H, F, Cl, CN or $C_1$–$C_6$alkyl, and $R_{20}$ is H, OH, $R_{11}$—H, F, Cl, CN, $R_{21}$—O—, $C_1$–$C_{12}$alkyl, —COO$^\ominus$, —COOR$_{10}$, —OCO—$R_{10}$, methylphenyl or phenyl, where $R_{21}$ is $C_1$–$C_{18}$alkyl, $C_5$–$C_7$cycloalkyl, ($C_1$–$C_{12}$alkyl)-$C_5$–$C_7$cycloalkyl, phenyl, ($C_1$–$C_{12}$alkyl)phenyl, benzyl or ($C_1$–$C_{12}$alkyl)benzyl.

$R_{18}$ is preferably H. Alkyl $R_{18}$ is preferably methyl or ethyl. If $R_{18}$ is —COOR$_{21}$, $R_{21}$ is preferably $C_1$–$C_{12}$alkyl, in particular $C_1$–$C_6$alkyl.

Alkyl $R_{19}$ is preferably $C_1$–$C_4$alkyl, for example methyl, ethyl, n-propyl or n-butyl. $R_{19}$ is preferably H, Cl or $C_1$–$C_4$alkyl.

If $R_{20}$ is the $R_{21}$—O— group, $R_{21}$ is preferably $C_1$–$C_{12}$alkyl, in particular $C_1$–$C_6$alkyl. Alkyl $R_{20}$ preferably contains 1 to 6, preferably 1 to 4, carbon atoms. If $R_{20}$ is the —COOR$_{21}$ group, $R_{21}$ is preferably $C_1$–$C_{12}$alkyl, in particular $C_1$–$C_6$alkyl, cyclopentyl or cyclohexyl. If $R_{20}$ is the —OCO—$R_{21}$ group, $R_{21}$ is preferably $C_1$–$C_{12}$alkyl, in particular $C_1$–$C_6$alkyl, phenyl or benzyl.

In a preferred embodiment, $R_{18}$ is H, $R_{19}$ is H, F, Cl, methyl or ethyl, and $R_{20}$ is H, OH, F, Cl, CN, $C_1$–$C_4$alkyl, $C_1$–$C_6$alkoxy, $C_1$–$C_6$hydroxyalkoxy, —COO—$C_1$–$C_6$alkyl, —OOC—$C_1$–$C_6$alkyl or phenyl.

Particular preference is given to oligomers and polymers in which $R_{18}$ is H, $R_{19}$ is H or methyl, and $R_{20}$ is H, OH, CN, methyl, $OCH_3$, $O(CH_2)_tOH$ or —$COOCH_3$, and t is an integer from 2 to 6.

A further preferred group of oligomers and polymers comprises partially or fully hydroxyalkylated oligo- or polyacrylates or methacrylates or -acrylamides or -methacrylamides in which the primary hydroxyl group or amino group has been substituted by radicals of the formula VII or VIIa. They can contain, for example, from 5 to 100 mol % of structural units of the formula XI

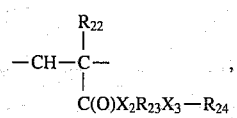  (XI)

and from 95 to 0 mol % of structural units of the formula XII

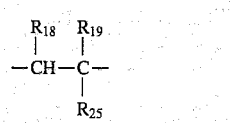  (XII)

in which $R_{22}$ is H or methyl, $X_2$ and $X_3$, independently of one another, are —O— or —NH—, $R_{23}$ is —$(CH_2)_c$—, and c is an integer from 2 to 12, preferably from 2 to 6, $R_{24}$ is a radical of the formula VII or VIIa, $R_{18}$ and $R_{19}$ are as defined above, and $R_{25}$ is as defined for $R_{20}$ or is —$C(O)X_2R_{23}X_3H$. The abovementioned preferences apply for $R_{24}$, $R_{18}$, $R_{19}$ and $R_{20}$. The abovementioned preferences apply for $X_2$ and $X_3$.

Other preferred oligomers and polymers are those made from polyalkylene oxides in which some or all of the H atoms of the terminal —OH or —$NH_2$ groups have been substituted by radicals of the formula VII or VIIa. These can be, for example, those of the formula XIII containing identical or different recurring structural units —[$CH_2CH(R_{27})$—O]—,

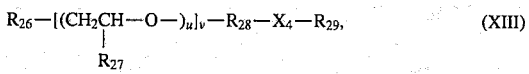  (XIII)

in which $R_{26}$ is the $R_{29}$—$X_4$— group or the v-valent radical of an alcohol or polyol having 1 to 20 carbon atoms, $R_{27}$ is H, $C_1$–$C_8$alkyl, preferably $C_1$–$C_4$alkyl, particularly preferably methyl, $R_{28}$ together with $X_4$ is a direct bond or $R_{28}$ is $C_2$–$C_6$alkylene, preferably $C_3$–$C_6$alkylene, particularly preferably 1,3-propylene, $X_4$ is —O— or —NH—, $R_{29}$ is a radical of the formula VII or VIIa, u has a numerical value of from 3 to 10 000, preferably from 5 to 5000, particularly preferably from 5 to 1000, especially preferably from 5 to 100, and v is an integer from 1 to 6, preferably from 1 to 4.

$R_{26}$ can be the monovalent to tetravalent radical of an alcohol or polyol. If $R_{26}$ is the radical of an alcohol, $R_{26}$ is preferably linear or branched $C_3$–$C_{20}$alkyl or -alkenyl, $C_3$–$C_8$-, particularly $C_5$–$C_6$cycloalkyl, —$CH_2$—($C_5$–$C_6$cycloalkyl), $C_6$–$C_{10}$aryl, in particular phenyl or naphthyl, or $C_7$–$C_{16}$aralkyl, in particular benzyl or 1-phenyl-2-ethyl. The cyclic or aromatic radicals may be substituted by $C_1$–$C_{18}$alkyl or $C_1$–$C_{18}$alkoxy.

If $R_{26}$ is the radical of a diol, $R_{26}$ is preferably branched and in particular linear $C_3$–$C_{20}$alkylene or -alkenylene and more preferably $C_3$–$C_{12}$alkylene, $C_3$–$C_8$-, in particular $C_5$–$C_6$cycloalkylene, —$CH_2$—($C_5$–$C_6$cycloalkyl)—, —$CH_2$—($C_5$–$C_6$ cycloalkyl)—$CH_2$—, $C_7$–$C_6$aralkylene, in particular benzylene, —$CH_2$—($C_6$–$C_{10}$aryl)—$CH_2$—, in particular xylylene. Cyclic or aromatic radicals may be substituted by $C_1$–$C_{12}$alkyl or $C_1$–$C_{12}$alkoxy.

If $R_{26}$ is a trivalent radical, it is derived from an aliphatic or aromatic triol. $R_{26}$ is preferably a trivalent aliphatic radical having 3 to 12 carbon atoms derived, in particular, from a triol, preferably containing primary hydroxyl groups. $R_{26}$ is particularly preferably —$CH_2(CH—)CH_2$—, $HC(CH_2—)_3$ or $CH_3C(CH_2—)_3$.

If $R_{26}$ is a tetravalent radical, it is preferably derived from an aliphatic triol. In this case $R_{26}$ is preferably $C(CH_2—)_4$.

The abovementioned preferences apply for $R_{29}$. Particular preference is given to homooligomers and homopolymers and block oligomers and polymers containing structural units of the formulae —[$CH_2CH_2$—O]— and —[$CH_2CH(CH_3)$—O—]—.

Also suitable are fluorinated polyethers which conform to the formula XIIIa

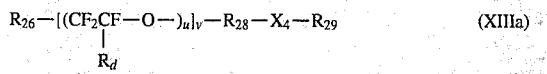  (XIIIa)

in which $R_{28}$, $R_{29}$, $X_4$, u and v are as defined above, $R_{26}$ is as defined above or is the monovalent radical of a partially or perfluorinated alcohol having 1 to 20, in particular 1 to 12, particularly preferably 1 to 6, carbon atoms, or the divalent radical of a partially or perfluorinated diol having 2 to 6, preferably 2 to 4, particularly preferably 2 or 3, carbon atoms, and $R_d$ is F or perfluoroalkyl having 1 to 12, preferably 1 to 6, particularly preferably 1 to 4, carbon atoms. $R_d$ is particularly preferably —$CF_3$.

Examples of other suitable oligomers and polymers are polyethyleneimines in which H atoms of the NH groups are substituted by radicals of the formulae V and/or Va, including the abovementioned preferences. Poly-ε-lysine is likewise suitable.

The oligomers and polymers according to the invention can be prepared in a simple manner known per se by reacting compounds of the formulae I and Ia with HO- or NH-functional oligomers and polymers. NH-functional oligomers and polymers are known in large number and are commercially available; their reaction with sugar acids gives the corresponding esters and amides containing a terminal polyhydroxyalkyl radical.

The photoinitiators of the formulae I and Ia according to the invention can also be used for the preparation of polymerizable photoinitiators containing ethylenically unsaturated groups by reacting the compounds of the formula I or Ia with OH- or NH-functional ethylenically unsaturated compounds. This reaction is known to the person skilled in the art and is not described in greater detail. Examples of OH- and NH-functional ethylenically unsaturated compounds are (hydroxyalkyl)- and (aminoalkyl)acrylic and -methacrylic esters and amides.

The invention furthermore relates to compounds of the formulae XIV and XIVa

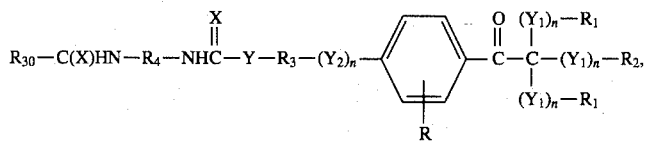
(XIV)

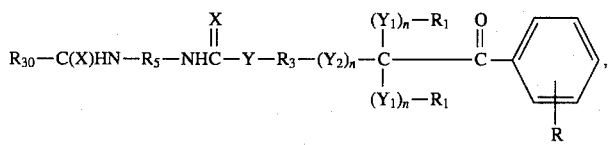
(XIVa)

in which X, Y, $Y_1$, $Y_2$, R, $R_1$, $R_2$, $R_3$, $R_4$, $R_5$ and n are as defined above, including the preferences, and $R_{30}$ is a radical of the formula XV

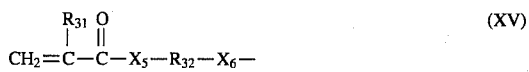
(XV)

in which $R_{31}$ is H or methyl, $R_{32}$ is branched or preferably linear $C_2$-$C_{12}$alkylene, and $X_5$ and $X_6$, independently of one another, are —O— or —NH—.

$R_{32}$ is preferably $C_2$-$C_6$alkylene, for example ethylene, 1,3-propylene, 1,4-butylene, 1,5-pentylene or 1,3-hexylene.

Some examples are:

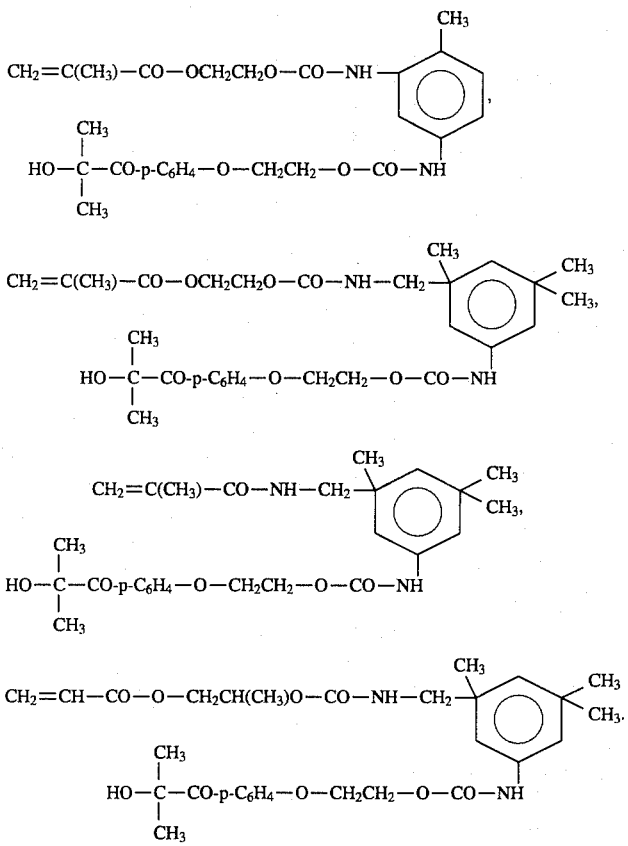

The compounds of the formulae I, Ia, XIV and XIVa are highly suitable as initiators for radiation-induced polymerization of ethylenically unsaturated compounds. In their specification, the compounds of the formulae XIV and XIVa are incorporated either as a whole or as fragments into the polymers, either via the unsaturated group and/or via the free-radicals formed. The oligomers and polymers according to the invention are likewise highly suitable as initiators, in which case graft polymers are formed or alternatively, depending on the content of initiator groups in the macroinitiator, penetrating polymer networks or those which are only bonded to one another to a partial extent, or not at all, can be formed.

The invention furthermore relates to a radiation-sensitive composition comprising a) an ethylenically unsaturated, photopolymerizable or photocrosslinkable compound (referred to as radiation-sensitive organic material below) and b) an amount, effective as initiator, of at least one compound of the formula I, Ia, XIV or XIVa or of an oligomer or polymer containing structural units of the formulae IV and IVa.

The compounds of component b) can be present in an amount of from 0.001 to 70% by weight, in particular from 0.001 to 50% by weight, especially from 0.01 to 40% by weight, very particularly from 0.01 to 20% by weight, based on component a). The amount depends principally on the photoactive groups bonded in the initiator; the fewer that are present, the larger the added amount selected.

Ethylenically unsaturated, photocrosslinkable compounds and thus also photostructurable materials are known. Such materials have been described, for example, by G. E. Green et al. in J. Macromol. Sci.; Revs. Macromol. and Chem., C21(2), 187–273 (1981 to 1982) and by G. A. Delzenne in Adv. Photothem., 11, pp. 1–103 (1979).

The radiation-sensitive organic material is preferably a non-volatile or low-volatility, monomeric, oligomeric or polymeric substance containing photopolymerizable, ethylenically unsaturated groups. Examples of photopolymerizable substances are acrylic and in particular methacrylic esters of alcohols and polyols, and acrylamides and in particular methacrylamides of amines and polyamines, for example $C_1$–$C_{18}$alkanols, ethylene glycol, propanediol, butanediol, hexanediol, di(hydroxymethyl)cyclohexane, polyoxyalkylenediols, for example di-, tri- or tetraethylene glycol, di- and tri-1,2-propylene glycol, trimethylolmethane, -ethane and -propane, and pentaerythritol, $C_1$–$C_{18}$alkylamines, ethylenediamine, diethylenetriamine and triethylenetetramine, which can be used alone, in mixtures or in blends with binders. Also suitable are mono-, oligo- and polysiloxanes with acrylic and particularly methacrylic esters bonded to pendant or terminal hydroxy($C_2$–$C_{12}$alkyl) or amino($C_2$–$C_{12}$alkyl)groups, for example 1-trimethylsilyl-3-methacroyloxypropane, 1-pentamethyldisiloxanyl-3-methacryloxypropane and 3-[tris(trimethylsiloxy)silyl]propyl methacrylate. Also suitable are perfluoroalkyl acrylates and methacrylates.

The photopolymerizable substances can contain further additives which are conventional for processing or use, and in addition other photoinitiators or photosensitizers.

The photopolymerization is carried out with exposure to radiation, preferably UV radiation, where known radiation sources can be employed, for example mercury vapour lamps.

The compounds of the formulae I and Ia can also be bonded to surfaces of inorganic and organic materials (referred to as substrates below) which contain H-active —COOH, —OH, —SH or —NH— groups. Suitable processes for this purpose are known, for example dipping, spraying, spreading, knife coating, pouring, rolling and in particular spin coating or vacuum vapour deposition processes. The compounds of the formulae I and Ia are firmly anchored to the surface by reaction with the isocyanate groups. This reaction can be carried out, for example, at elevated temperatures, for example at from 40° to 100° C. After the reaction, excess compounds can be removed, for example using solvents. Photopolymerizable substances can then be applied to the modified surfaces and subsequently polymerized by exposure to radiation and firmly bonded to the substrate by graft polymerization via the photoinitiators. In this case, a tentacle-like or brush-like polymer structure forms on the substrate surface.

Examples of suitable substrates are glasses, silicate minerals (silica gels), metal oxides and in particular natural or synthetic polymers, which are known in large number. Some examples of polymers are polyaddition and polycondensation polymers (polyurethanes, epoxy resins, polyethers, polyesters, polyamides and polyimides); vinyl polymers (polyacrylates, polymethacrylates, polystyrene, polyethylene and halogenated derivatives thereof, polyvinyl acetate and polyacrylonitrile); elastomers (silicones, polybutadiene and polyisoprene); modified or unmodified biopolymers (collagen, cellulose, chitosan and the abovementioned biopolymers). If substrates contain too few or no functional groups, the substrate surface can be modified by methods known per se, for example plasma methods, and functional groups such as —OH, —$NH_2$ or —$CO_2H$ produced. Particularly preferred substrates are contact lenses.

The invention furthermore relates to a material comprising (a) an inorganic or preferably organic substrate to which is bonded (b), as photoinitiator, at least one compound of the formula I or Ia, which is strongly bonded to the substrate via O atoms, S atoms, N—$C_1$–$C_6$alkyl groups or NH groups on the one hand and the isocyanate group of the photoinitiators on the other hand, and, if desired, (c) a thin coating of a polymer on the photoinitiator layer, this polymer being obtainable by applying a thin coating of photopolymerizable, ethylenically unsaturated substances to the substrate surface provided with photoinitiator radicals, and polymerizing the coating of ethylenically unsaturated substances by irradiation, preferably with UV radiation.

This material is preferably an ophthalmic moulding made from a transparent organic base material, for example a contact lens or an intraocular lens, particularly preferably a contact lens.

The coating thickness of the ethylenically unsaturated substances depends principally on the desired properties. It can be from 0.001 μm to 1000 μm, preferably from 0.01 μm to 500 μm, particularly preferably from 0.01 to 100 μm, especially preferably from 0.5 to 50 μm, very particularly preferably from 1 to 20 μm. For the production of contact lenses in particular, a coating thickness of from 0.5 to 5 μm is desired. The coating can be produced by the abovementioned coating methods.

The ethylenically unsaturated substances can be the abovementioned compounds. Other suitable ethylenically unsaturated compounds are non-volatile substituted polyolefins, in particular acrylic acid and methacrylic acid, and esters and amides thereof, for example $C_1$–$C_{12}$alkyl or oligooxaalkylene or $C_1$–$C_{12}$hydroxyalkyl acrylates or methacrylates or acrylamides or methacrylamides (2,3-dihydroxypropyl methacrylate, N,N-dimethylacrylamide, acrylamide, N,N-diethylaminoethyl methacrylate, oligoethylene oxide acrylates and methacrylates, 2-hydroxyethylmethacrylic esters), and N-vinylpyrrolidone.

The invention furthermore relates to a process for modifying surfaces of inorganic or organic substrates containing H-active HO—, HS—, HN—$C_1$–$C_6$alkyl or —$NH_2$ groups, comprising the steps a) application of a thin coating of photoinitiators of at least one compound of the formulae I and Ia to the substrate, if desired together with a catalyst, for example dibutyltin laurate, b) if necessary warming the coated material and washing off the excess photoinitiator, c) application of a thin coating of photopolymerizable, ethylenically unsaturated substances to the substrate surface provided with photoinitiator radicals, and d) polymerization of the coating of ethylenically unsaturated substances by irradiation, preferably with UV radiation.

Any non-covalently bonded polymers formed can be removed after the polymerization, for example by treatment with suitable solvents.

The process according to the invention can be used to modify the surfaces in a variety of ways and to provide the surfaces with particular properties for various applications.

Depending on the choice of the ethylenically unsaturated substances, it is possible, for example, specifically to improve mechanical properties, for example the surface hardness, scratch resistance, wettability, abrasion resistance and writability, and physical properties, for example the coefficient of friction, the permeability to gases, liquids and dissolved inorganic or organic substances of low to high molecular weight, and the optical transparency, particularly strong adhesion of the polymer coatings being a particular advantage.

The photoinitiators according to the invention and the substrates modified by means of the photoinitiators are distinguished by high chemical and photochemical reactivity. They can be used to produce photoreactive materials, which can be used as coating materials, photostructurable materials, for composite materials and in particular as materials for biomedical applications, for example contact lenses and surgical materials. The materials are particularly suitable for the production of hydrophilic and biocompatible surfaces on contact lenses by graft polymerization with formation of a tentacle structure (brush structure) which is particularly suitable for the required properties.

Of particular importance are the high wettability and the fact that a stable moisture film is obtained on the surface, for example a tear film on the surface of a contact lens. Furthermore, the improvement in the behaviour in biological systems is of considerable importance, for example improved biocompatibility, protection against bioerosion, prevention of plaque formation and of biofouling, and no blood coagulation or toxic or allergic reactions.

The modified materials according to the invention are particularly suitable for the production of contact lenses. With respect to contact lenses, the following property improvements are particularly important: high wettability (small contact angle), high tear strength, good lubrication effect, high abrasion resistance, only insignificant enzymatic degradation, or none at all, no deposition of components from the tear fluid (proteins, lipids, salts and cell degradation products), no affinity to cosmetics, volatile chemicals, for example solvents, dirt and dust, and no attachment or lodging of microorganisms.

The modified materials according to the invention are also suitable for the production of artificial blood vessels and other biomedical materials for prostheses, for surgery and for diagnostics, where it is particularly advantageous that endothelial cells can grow over them.

The invention furthermore relates to a contact lens comprising (a) a transparent, organic base material containing functional groups, in particular hydroxyl, mercapto, amino, alkylamino or carboxyl groups, and (b) a thin surface coating comprising (b1) at least one photoinitiator of the formula I or Ia and (b2) a graft polymer formed by photopolymerization of a non-volatile or low-volatility olefin.

Examples of suitable base materials are modified or unmodified natural polymers, for example collagen, chitosan, hyaluronic acid and cellulose esters, such as cellulose acetate or cellulose butyrate, modified or unmodified synthetic polymers, for example polyvinyl alcohol, polyhydroxyethyl methacrylate, polyglyceryl methacrylate, and copolymers based on these polymers. Also suitable are natural and synthetic polymers, for example polymers containing silicone, perfluoroalkyl and/or alkyl acrylate structural units, in which functional groups can be produced on the surface by means of suitable methods, for example plasma treatment, etching or oxidation.

Examples of suitable non-volatile or low-volatility olefins are acrylamide, N,N-dimethylacrylamide, methacrylamide, hydroxyethyl methacrylate, glyceryl methacrylate, oligoethylene oxide mono- and bisacrylates, ethylene glycol dimethacrylate, methylenebisacrylamide, vinylcaprolactam, acrylic acid, methacrylic acid, monovinyl fumarate, vinyl trifluoroacetate and vinylene carbonate.

The examples below illustrate the invention in greater detail.

A) Preparation examples

EXAMPLE A1

Preparation of

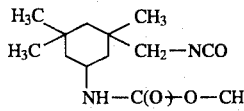

NH—C(O)—O—CH$_2$CH$_2$—O-p-C$_6$H$_4$—C(O)—C(CH$_3$)$_2$—OH

In a 500 ml flask fitted with reflux condenser, thermometer, stirrer and nitrogen inlet tube, a solution of 11.125 g (0.05 mol) of freshly distilled isophorone diisocyanate (IPDI) in 50 ml of dry methylene chloride is mixed under nitrogen with a solution of 11.2 g (0.05 mol) of 4'-(β-hydroxyethoxy)-2-hydroxyprop-2-ylphenone (Darocure 2959®) in 300 ml of dry methylene chloride, 20 mg of dibutyltin dilaurate are added as catalyst, and the mixture is stirred at room temperature for 48 hours. The course of the reaction is monitored by thin-layer chromatography on silica-gel plates (60 F$_{254}$, Art. 5719, Merck) (mobile phase: toluene/acetonitrile 7:3). The product obtained is freed from small amounts of unreacted Darocure 2959 and disubstituted IPDI by column chromatography on silica gel 60 (eluent toluene/acetonitrile 7:3). The pure fractions are evaporated on a rotary evaporator, giving a colourless oil, which crystallizes slowly on cooling to −16° C. and is subsequently recrystallized from dry diethyl ether, giving 15.6 g of a white crystalline product (70% of theory), which has a melting point of 76° C.

The isocyanate content of the product is determined by titration with dibutylamine in toluene: calculated 2.242 meq/g, found 2.25 meq/g.

The method is described in "Analytical Chemistry of Polyurethanes" (High Polymer Series XVI/Part III, D. S. David+H. B. Staley, editors, Interscience Publishers, New York, 1969, p. 86).

EXAMPLE A2

Preparation of

OCNCH$_2$C(CH$_3$)$_2$CH$_2$CH(CH$_3$)(CH$_2$)$_2$NHC(O)O(CH$_2$)$_2$O 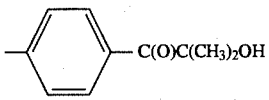 C(O)C(CH$_3$)$_2$OH Analogously to Example A1, 10.5 g (0.05 mol) of 1,6-diisocyanato-2,2,4-trimethylhexane (TMDI) are reacted with 11.1 g (0.05 mol) of Darocure 2959® in 400 ml of dry methylene chloride at room temperature under nitrogen for 40 hours. 14.5 g (67% of theory) of a white, crystalline

EXAMPLE A3

Preparation of

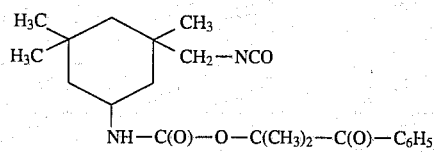

NH—C(O)—O—C(CH$_3$)$_2$—C(O)—C$_6$H$_5$

Analogously to Example A1, 11.125 g (0.05 mol) of IPDI in 15 ml of dry methylene chloride are reacted with 8.2 g (0.05 mol) of 2-hydroxyprop-2-ylphenone (Darocure 1173®). The reaction mixture is first stirred at room temperature for 24 hours and subsequently heated at 30° C. for 24 hours and at 45° C. for 48 hours. After the solvent has been evaporated, the product is purified by chromatography on silica gel 60 using toluene/acetone 7:1 as eluent, giving 12.5 g (70% of theory) of a white, crystalline product which has a melting point of 100°–102° C.

NCO titration: calculated 2.58 meq/g, found 2.52 meq/g.

EXAMPLES A4–A6

Analogously to Example A3, further photoinitiators are reacted with diisocyanates in 250 ml of CH$_2$Cl$_2$. The results are shown in Table 1. IRGACURE 184® is 1-hydroxycyclohex-1-ylphenone.

EXAMPLE A7

Preparation of

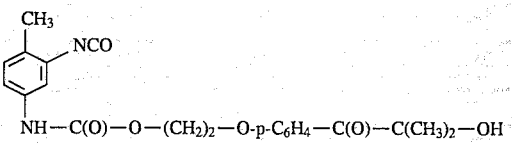

NH—C(O)—O—(CH$_2$)$_2$—O-p-C$_6$H$_4$—C(O)—C(CH$_3$)$_2$—OH

In the apparatus described in Example A1, 1.74 g (0.01 mol) of tolylene 2,4-diisocyanate (TDI) in 20 ml of dichloromethane are reacted with 2.24 g (0.01 mol) of Darocure 2959® dissolved in 60 ml of dry dichloromethane. The reaction mixture, without addition of a catalyst, is stirred at room temperature for 48 hours and at 40° C. for 1 hour until unreacted Darocure 2959 can no longer be detected in the thin-layer chromatogram. The product is isolated by precipitation of the reaction solution in 180 mol of dry petroleum ether (b.p. 40°–60° C.) and is subsequently recrystallized twice from dichloromethane/petroleum ether 1:3.

A white, crystalline product of melting point 124°–125° C. is obtained. Yield 17.2 g, corresponding to 87% of theory. OCN titration: calculated 2.50 meq/g, found 2.39 meq/g.

EXAMPLES A8–A10

Analogously to Example A7, tolylene diisocyanate is reacted with various photoinitiators in 40 ml of petroleum ether. The results are shown in Table 2.

TABLE 1

| Example | Isocyanate | Photo-initiator | Yield | Melting point (°C.) | OCN titration [meq/g] |
|---|---|---|---|---|---|
| A4 | TMDI 10.5 g (0.05 mol) | Darocure 1173 ® 8.2 g (0.05 mol) | 12.5 g [67% of theory] | colourless oil | Calculated 2.67 Found 2.52 |
| A5 | IPDI 11.125 g (0.05 mol) | Irgacure 184 ® 10.25 g (0.05 mol) | 17.5 g [82% of theory] | 121–123 | Calculated 2.34 Found 2.30 |
| A6 | TMDI 10.5 g (0.05 mol) | Irgacure 184 ® 10.25 g (0.05 mol) | 14.1 g [68% of theory] | colourless oil | Calculated 2.41 Found 2.27 |

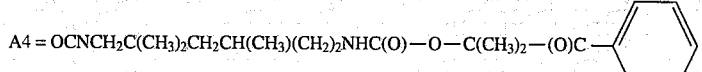

A4 = OCNCH$_2$C(CH$_3$)$_2$CH$_2$CH(CH$_3$)(CH$_2$)$_2$NHC(O)—O—C(CH$_3$)$_2$—(O)C—

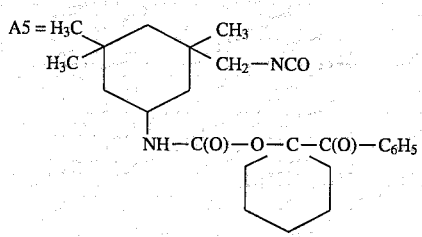

A5 =

A6 = OCNCH$_2$C(CH$_3$)$_2$CH$_2$CH(CH$_3$)(CH$_2$)$_2$NHC(O)—O—C—C(O)—C$_6$H$_5$

TABLE 2

| Example | Isocyanate | Photoinitiator | Yield | Melting point (°C.) | OCN titration [meq/g] |
|---|---|---|---|---|---|
| A8 | TDI 2.61 g (0.015 mol) | Darocure 1173 ® 1.6 g (0.01 mol) | 2.8 g (83% of theory) | 177–178 | Calculated 2.95 Found 2.95 |
| A9 | TDI 2.61 g (0.015 mol) | Irgacure 184 2.0 g (0.01 mol) | 3.33 g (88% of theory) | 225–226 | Calculated 2.64 Found 2.59 |
| A10 | TDI 2.61 g (0.015 mol) | Benzoin 2.12 g (0.01 mol) | 3.73 g (79% of theory) | 229–232 | Calculated 2.59 Found 2.95 |

A8 = 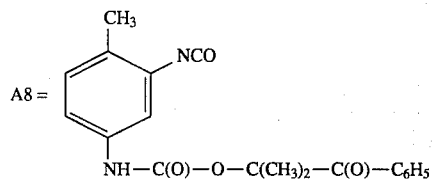

A9 = 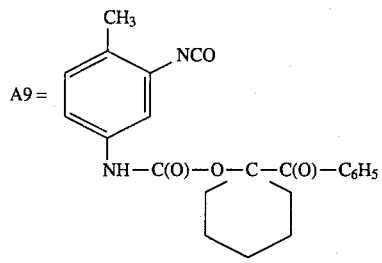

A10 = 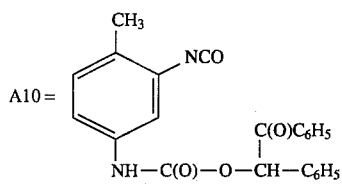

B) Preparation of macrophotoinitiators

EXAMPLE B1

Preparation of

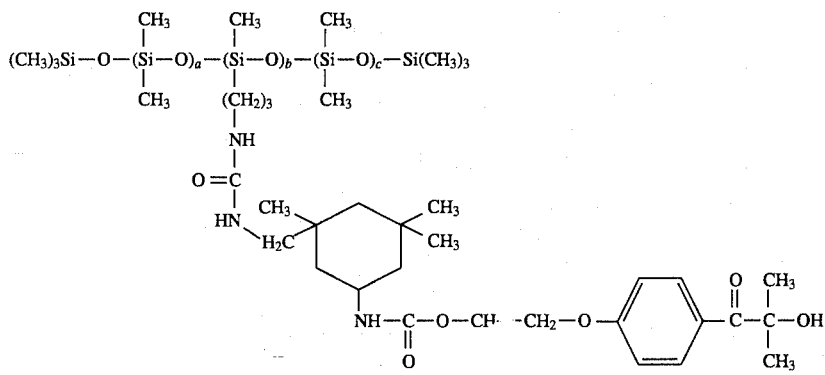

In a 250 ml flask as described in Example A1, a solution of 1 g of the compound of Example A1 (0.00224 mol) in 50 ml of dry dichloromethane is reacted with 4.37 g of aminoalkylpolysiloxane (0.515 meq of $NH_2$/g, Petrarch PS 813®: $\overline{M}n$~3000, b=3, a+c=37) dissolved in 100 ml of dry dichloromethane. The reaction mixture is stirred at room temperature for 10 hours and subsequently warmed at 40° C. for 1 hour. After the mixture has been cooled, the solvent is removed by evaporation on a rotary evaporator, giving a highly viscous, colourless oil, which is finally freed from traces of the solvent in a high vacuum at 40° C. and $10^{-4}$ mmHg. Yield 5.34 g, corresponding to 99.5% of theory. The product no longer shows an OCN band in the IR spectrum.

EXAMPLES B2–B6

Analogously to Example B1, further amino-functional macromers are reacted with the compound described in Example A1. The results are shown in Table 3.

TABLE 3

| Example | Aminofunctional macromer | Compound of Ex. A1 | Structure (Product) | Yield | % N (Calculated/ found) |
|---|---|---|---|---|---|
| B2 | X-22-161c (Shin Etsu, JP) 7.8 g (0.43 meq NH$_2$/g) $\bar{M}$ ~ 4600 | 1.5 g (3.36 mmol) | a | 9.2 g (99.6%) | 1.52/1.42 |
| B3 | Jeffamin ® T 403 (Texaco, USA) 2.8 g (6.38 meq NH$_2$/g) | 2.84 g (6.36 mmol) | b | 5.62 g (99.7%) | 7.08/7.11 |
| B4 | Jeffamin ® D2000 (Texaco, USA) 4.0 g (1 meq NH$_2$/g) | 1.786 g (2.0 mmol) | c | 5.78 g (99.9%) | 2.90/2.89 |
| B5 | KF-8003 (Skin Etsu, JP) 4.6 g (0.49 meq NH$_2$/g) | 1.0 g (2.29 mmol) | d | 4.55 g (98.9%) | 1.63/1.58 |
| B6 | X-22-161B (Shin Etsu, JP) 3.23 g (0.699 meq NH$_2$/g) $\bar{M}$ ~ 2900 | 1.0 g (2.29 mmol) | e | 4.2 g (99.3%) | 2.23/2.09 |

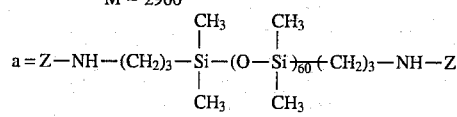

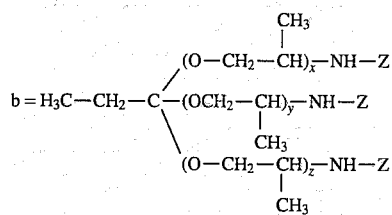

x + y + z = 5–6

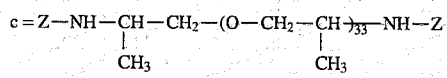

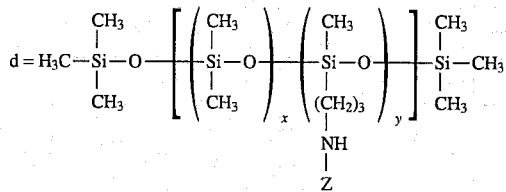

x:y = 27:1

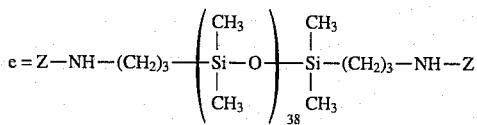

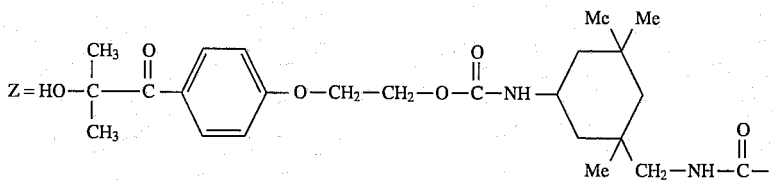

EXAMPLE B7

Preparation of

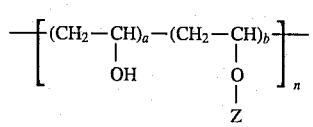

a:b ≈ 30:1
n ≈ 10

In the apparatus described in Example A1, 2.1 g of polyvinyl alcohol (PVA) (Serra® 03/20 $\bar{M}$n~13 000) are dissolved under nitrogen in 50 ml of dry N-methyl-2-pyrrolidone (NMP) at 90° C. The solution is cooled to room temperature and filtered through a G4 glass frit, and the solution of 0.7 g (1.567 mmol) of the compound of Example A1 in 10 ml of dry NMP is added. 10 mg of dibutyltin dilaurate are added, and the reaction mixture is stirred at 50° C. for 48 hours. After this reaction time, IR spectroscopy shows no evidence of unreacted diisocyanate (OCN at 2280 cm$^{-1}$). After the mixture has been cooled to room temperature, the product is precipitated in 400 ml of dry diethyl ether, filtered off, washed with dry diethyl ether and dried in vacuo, giving 2.6 g of a white product containing 1.38% of nitrogen. $^1$H chemical shifts of aromatic protons of the photoinitiators bonded to PVA: $\delta$7.00–7.10 (d, 2H); $\delta$8.15–8.25 (d, 2H).

EXAMPLE B8

Reaction of hyaluronic acid with the reactive photoinitiator from Example A1.

Analogously to Example B7, 444 mg of hyaluronic acid (Denki Kagaku Kogyo, $\overline{M}n$~1.2×10$^6$), dissolved in 100 ml of dry dimethyl sulfoxide (DMSO), are reacted at 50° C. with a solution of 200 mg of the compound described in Example 1 in 10 ml of dry DMSO, giving 534 mg (82.7% of theory) of a white product which carries a photoinitiator group bonded as urethane or carboxamide on about 30% of the sugar radicals in the main polymer chain, as shown by evaluation of the $^1$H-NMR spectrum. $^1$H chemical shifts of aromatic protons of the photoinitiators bonded to hyaluronic acid: $\delta$7.00–7.10 (d, 2H); $\delta$8.15–8.25 (d, 2H).

EXAMPLES B9–B11

Analogously to Example B8, the reactive photoinitiator described in Example A1 is reacted with some hydroxyalkyl-substituted polydimethylsiloxanes in dichloromethane as solvent. The results are shown in Table 4.

TABLE 4

| Example | Photo-initiator from Ex. 1 | Polysiloxane | Yield | Elemental analysis % calculated/found |
|---|---|---|---|---|
| B9 | 1.0 g (2.25 mmol) | KF-6002 (Shin Etsu, JP) 3.6 g (0.625 meq OH/g) | 4.55 g | C 39.87/39.86 (98.9%) H 7.96/8.29 N 1.36/1.04 |
| B10 | 1.0 g (2.23 mmol) | KF-6001 (Shin Etsu, JP) 2.05 g (1.1 meq OH/g) | 3.0 g | C 23.49/24.11 (98.3%) H 8.12/8.54 N 2.03/1.79 |
| B11 | 1.0 g (2.25 mmol) | Gluconamidopropyl-methyldimethylsiloxane copolymer 4.55 g (6.495 meq OH/g) | 4.8 g (86.5%) | C –/36.18 H –/8.08 N –/1.03 |

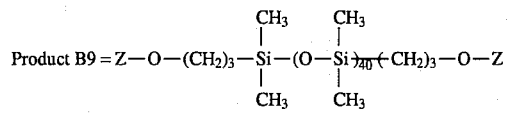

Product B9 = Z—O—(CH$_2$)$_3$—Si(CH$_3$)$_2$—(O—Si(CH$_3$)$_2$)$_{40}$—(CH$_2$)$_3$—O—Z

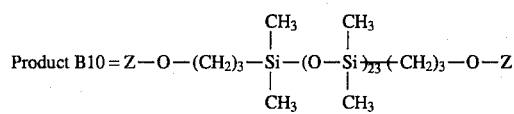

Product B10 = Z—O—(CH$_2$)$_3$—Si(CH$_3$)$_2$—(O—Si(CH$_3$)$_2$)$_{23}$—(CH$_2$)$_3$—O—Z

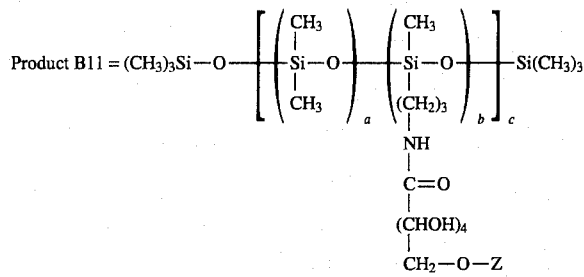

Product B11 structure with a:b = 12:1, c = 3

EXAMPLE B12

Cyclodextrin macroinitiator

Cyclodextrins are cyclic oligosaccharides of the formula

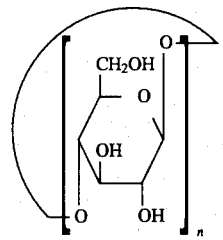

in which n is a number from 6 to 8. They are commercial and hydroxyalkylated derivatives having a degree of substitution of from 0.6 to 1.6 per dextrin unit.

The reaction with the photoinitiators according to the invention generally gives mixtures comprising derivatives having various substitution patterns and various degrees of substitution. The preferred point of substitution is the primary hydroxyl group. The mixtures can be separated by chromatography, where $C_6$ monosubstituted derivatives with 6 to 8 photoinitiators can readily be separated off. 5 g (4.4053 mmol) of dry β-cyclodextrin and 0.094 g of dibutyltin laurate are dissolved under dry nitrogen in 50 ml of dry dimethyl sulfoxide in a 250 ml flask made of brown glass fitted with reflux condenser, stirrer, internal thermometer and dropping funnel. A solution of 13.77 g (3.084 mmol) of the compound of Example A1 in 50 ml of dry dimethyl sulfoxide is added dropwise to this solution at room temperature. The mixture is stirred first at room temperature for 3 hours and subsequently at 50° C. for 15.5 hours, after which unreacted β-cyclodextrin can no longer be detected by chromatography. The reaction mixture is cooled, and the product is precipitated by addition of 1000 ml of dry diethyl ether. The isolated, viscous product is dissolved in 25 ml of acetone and re-precipitated by means of 500 ml of diethyl ether, giving a white suspension. The product is filtered off, and the white powder obtained is washed twice with 100 ml of diethyl ether and subsequently dried in vacuo with exclusion of light, giving 13.04 g (53.5% of theory) of product. The nitrogen content of 3.73% corresponds to a mean degree of substitution of 5.6 per cyclodextrin ring. The product is fractionated by flash chromatography (column 60 cm in length, 5 cm in diameter) on silica gel (Merck 60 F, grain size 0.04 to 0.063 mm) using methanol/toluene (2:8) as eluent. With 13 g of crude product, the following fractions are obtained, fraction 2 being eluted with pure methanol and fraction 3 with methanol/water (1:1):

| Fraction | Amount (g) | N content (%) | Mean degree of substitution |
|---|---|---|---|
| 1 | 1.3 | 4.25 | 6.4 |
| 2 | 3.59 | 3.59 | 5.4 |
| 3 | 1.36 | 1.36 | 2.0 |

C) Surface reaction of polymer films with the reactive photoinitiator described in Example A1.

EXAMPLES C1–C5

Films of various polymer materials containing reactive groups are wetted on the surface with the solution of the photoinitiator prepared as described in Example A1 in a suitable solvent (concentration ~20% by weight) by dipping, spraying or brushing. The films treated in this way are heated at 60° C. for 24 hours under dry nitrogen and subsequently freed from unreacted photoinitiator by washing with acetone. After drying in the absence of light, the films are analysed by FTIR microscopy.

| Example | Polymer film | Mn | Solvent | IR bands (cm$^{-1}$) |
|---|---|---|---|---|
| C1 | Polyvinylalcohol | ~70000 | DMSO | (Ar C=C) 1600, 1510 (C=O) 1695 |
| C2 | Chitosan | ~145000 | DMSO | (Ar C=C) 1600, 1510 (C=O) 1690 |
| C3 | Collagen | ~80000 | DMSO | (Ar C=C) 1600, 1510 (C=O) 1695 |
| C4 | Polyvinylalcohol containing 1% of TMDI | — | MEK + 1% DMSO | (Ar C=C) 1600 (C=O) 1705 |
| C5 | Gluconamidopropymethyldimethylsiloxane copolymer, crosslinked with IPDI (20% OH groups) | ~4000 | MEK + 1% DMSO | (Ar C=C) 1600, 1510 (C=O) 1700 |

MEK = methyl ethyl ketone

EXAMPLE C6

Surface reaction of a contact lens

Contact lenses of crosslinked polyhydroxyethyl methacrylates (poly-HEMA) are wetted on the surface with a solution of compound A1 in tetrahydrofuran (concentration 5%) or diethyl ether. The treated contact lenses are stored at room temperature for 16 hours under dry nitrogen, then washed with acetone for 8 hours and then dried in a high vacuum.

D) Surfaces—graft polymerization with the modified polymer films produced as in Examples C1–C4 and N-vinyl-2-pyrrolidone

EXAMPLES D1–D4

The polymer films of Examples C1–C4 are wetted with freshly distilled N-vinyl-2-pyrrolidone by dipping, spraying or brushing, freed from oxygen by repeated evacuation and introduction of $N_2$ gas and exposed to UV radiation from a mercury high pressure lamp in an $N_2$ atmosphere (photoresist exposure machine 82420, Oriel). The films are subsequently washed several times with methanol in order to remove unpolymerized N-vinyl-2-pyrrolidone and unbonded homopolymer. The films are dried in vacuo and analysed by FTIR spectroscopy (IR bands of NVP).

| Example | UV irradiation | FTIR bands (cm$^{-1}$) duration | | | |
|---|---|---|---|---|---|
| D1 | 20 minutes | 1510, 1600 } | (C=C Ar); | 1660 (C=O), 1440–1470 } | NVP |
| D2 | 30 minutes | 1510, 1600 } | (C=C Ar); | 1660 (C=O) | NVP |
| D3 | 15 minutes | 1600 | (C=C Ar); | 1660 (C=O) | NVP |
| D4 | 40 minutes | 1600 | (C=C Ar); | 1675 (C=O), 1400–1450 } | NVP |

Ar = aromatic, NVP = N-vinylpyrrolidone

EXAMPLE D6

Modification of the surface of a contact lens.

Contact lenses treated as described in Example C6 are immersed in an aqueous solution of acrylamide and then freed from oxygen by repeated evacuation and interaction of nitrogen. The lenses are then irradiated twice for 2 minutes under nitrogen by means of a mercury high-pressure lamp (photoresist exposure machine 82420, Oniel, 2000 W). The contact lenses are then washed with distilled water and dried in a high vacuum. The contact lenses have the following values for the contact angle and contact angle hysteresis before (poly-HEMA) and after the treatment. The data show the good reproducibility.

| Product | Advancing angle | Receding angle | Hysteresis |
|---|---|---|---|
| Poly-HEMA | 78° | 33° | 44° |
| Lens 1 from Example D6 | 54° | 49° | 5° |
| Lens 2 from Example D6 | 49° | 41° | 8° |
| Lens 3 from Example D6 | 53° | 48° | 5° |

What is claimed is:

1. A compound of formula I:

$$XCN-R_4-NHC(X)-Y-R_3-(Y_2)_n-\text{Ar}(R)-C(O)-C((Y_1)_n-R_1)((Y_1)_n-R_1)((Y_1)_n-R_2)$$

in which X is O; Y is O, NH or NR$_6$; Y$_1$ is O; Y$_2$ is —O—, —O—(O)C—, —C(O)—O— or —O—C(O)—O—; the n indices, independently of one another, are 0 or 1; R is H, C$_1$–C$_{12}$ alkyl, C$_1$–C$_{12}$ alkoxy or C$_1$–C$_{12}$ alkyl-NH—; the R$_1$ and R$_2$ radicals, independently of one another, are H, linear or branched C$_1$–C$_8$ alkyl, C$_1$–C$_8$ hydroxyalkyl, C$_6$–C$_{10}$ aryl, or two groups R$_1$—(Y$_1$)$_n$— together are —(CH$_2$)$_x$—, or the R$_1$—(Y$_1$)$_n$— and R$_2$—(Y$_1$)$_n$— groups together form a radical of the formula $$\begin{array}{c} R_a \diagdown \diagup R_b \\ O \quad O \\ \diagdown CH_2 \diagup \end{array}$$

R$_3$ is a direct bond or linear or branched C$_1$–C$_8$ alkylene, which is unsubstituted or substituted by —OH and/or is uninterrupted or interrupted by one or more —O—, —O—C(O)— or —O—C(O)—O— groups;

R$_4$ is a branched C$_3$–C$_{18}$ alkylene, C$_6$–C$_{10}$ arylene, which is unsubstituted or substituted by C$_1$–C$_4$ alkyl or C$_1$–C$_4$ alkoxy, C$_7$–C$_{18}$ aralkylene which is unsubstituted or substituted by C$_1$–C$_4$ alkyl or C$_1$–C$_4$ alkoxy, C$_3$–C$_8$ cycloalkylene which is substituted by C$_1$–C$_4$ alkyl or C$_1$–C$_4$ alkoxy, C$_3$–C$_8$ cycloalkylene-C$_y$H$_{2y}$— which is unsubstituted or substituted by C$_1$–C$_4$ alkyl or C$_1$–C$_4$ alkoxy, or —C$_y$H$_{2y}$—(C$_3$–C$_8$ cycloalkylene)—C$_y$H$_{2y}$ which is unsubstituted or substituted by C$_1$–C$_4$ alkyl or C$_1$–C$_4$ alkoxy;

R$_6$ is a linear or branched C$_1$–C$_6$ alkyl;

x is an integer from 3 to 5;

y is an integer from 1 to 6;

R$_a$ and R$_b$, independently of one another, are H, C$_1$–C$_8$ alkyl, C$_3$–C$_8$ cycloalkyl, benzyl or phenyl;

with the provisos that n in the —(Y$_1$)$_n$—R$_1$ groups is 0 if R$_2$ is H; that at most two Y$_1$ radicals in the —(Y$_1$)$_n$— groups in the formula I are O and n in the other —(Y$_1$)$_n$— groups is 0; R$_4$ provides different reactivity to the two NCX groups; and that n in the —(Y$_2$)$_n$— groups is 0 if R$_3$ is a direct bond.

2. A compound according to claim 1, wherein Y is O.

3. A compound according to claim 1, wherein Y$_2$ is O.

4. A compound according to claim 1, wherein R is C$_1$–C$_6$alkyl or C$_1$–C$_6$alkoxy.

5. A compound according to claim 1, wherein R is C$_1$–C$_4$alkyl or C$_1$–C$_4$alkoxy.

6. A compound according to claim 1, wherein R is H.

7. A compound according to claim 1, wherein the alkyl and alkoxy substituents are methyl, ethyl, methoxy or ethoxy.

8. A compound according to claim 1, wherein alkyl R$_1$ is linear C$_1$–C$_4$alkyl.

9. A compound according to claim 8, wherein R$_1$ is methyl or ethyl.

10. A compound according to claim 1, wherein aryl R$_1$ is phenyl.

11. A compound according to claim 1, wherein both R$_1$—(Y$_1$)$_n$— groups are —(CH$_2$)$_x$—, in which x is 4 or 5.

12. A compound according to claim 1, wherein R$_2$ is H, methyl or ethyl.

13. A compound according to claim 1, wherein R$_1$ is ethyl or methyl or the two R$_1$—(Y$_1$)$_n$— groups together are pentamethylene, n in the —(Y$_1$)$_n$—R$_2$ group is 0, R$_2$ is methyl or H, and R is H.

14. A compound according to claim 1, wherein, in the —(Y$_1$)$_n$—R$_2$ group, Y$_1$ is O, n is 1 and R$_2$ is H.

15. A compound according to claim 1, wherein, in the —(Y$_1$)$_n$—R$_2$ group, Y$_1$ is O, n is 1 and R$_2$ is H, and n in the R$_1$—(Y$_1$)$_n$— groups is 0.

16. A compound according to claim 1, wherein R$_3$ is alkylene of 1 to 4 carbon atoms.

17. A compound according to claim 1, wherein R$_3$ is ethylene, or R$_3$ is a direct bond and n in the —(Y$_2$)$_n$— group is 0.

18. A compound according to claim 1, wherein $R_4$ is branched $C_4$–$C_{10}$alkylene.

19. A compound according to claim 18, wherein $R_4$ is 2,2-dimethyl-1,4-butylene, 2,2-dimethyl-1,5-pentylene, 2,2,3- or 2,2,4-trimethyl-1,5-pentylene, 2,2-dimethyl-1,6-hexylene, 2,2,3- or 2,2,4- or 2,2,5-trimethyl-1,6-hexylene, 2,2-dimethyl-1,7-heptylene, 2,2,3- or 2,2,4- or 2,2,5- or 2,2,6-trimethyl-1,7-heptylene, 2,2-dimethyl-1,8-octylene, 2,2,3- or 2,2,4- or 2,2,5- or 2,2,6- or 2,2,7-trimethyl-1,8-octylene.

20. A compound according to claim 1, wherein $R_4$ is selected from the group consisting of phenylene, naphthylene, phenylene which is substituted in the ortho-position to the XCN group by $C_1$–$C_4$ alkyl or $C_1$–$C_4$ alkoxy, and naphthylene which is substituted in the ortho-position to the XCN group by $C_1$–$C_4$ alkyl or $C_1$–$C_4$ alkoxy, and naphthylene.

21. A compound according to claim 20, wherein $R_4$ is 1-methyl-2,4-phenylene, 1,5-dimethyl-2,4-phenylene, 1-methoxy-2,4-phenylene or 1-methyl-2,7-naphthylene.

22. A compound according to claim 1, wherein $R_4$ is phenylalkylene having 1 to 6 carbon atoms in the alkylene group.

23. A compound according to claim 1, wherein $R_4$ is $C_5$- or $C_6$-cycloalkyl which is unsubstituted or methyl substituted $C_5$- or $C_6$ cycloalkyl.

24. A compound according to claim 23, wherein $R_4$ is 1,3-cyclopentylene, 1,3- or 1,4-cyclohexylene, 4-methyl-1,3-cyclopentylene, 4-methyl-1,3-cyclohexylene, 4,4-dimethyl-1,3-cyclohexylene, 3-methyl- or 3,3-dimethyl-1,4-cyclohexylene, 3,5-dimethyl-1,3-cyclohexylene or 2,4-dimethyl-1,4-cyclohexylene.

25. A compound according to claim 1, wherein —$R_4$ is cyclohexylene-$C_yH_{2y}$— which is unsubstituted or substituted by 1 to 3 $C_1$–$C_4$alkyl groups.

26. A compound according to claim 25, wherein the —$C_yH_{2y}$— group is methylene.

27. A compound according to claim 25, wherein $R_4$ is cyclopent-1-yl-3-methylene, 3-methylcyclopent-1-yl-3-methylene, 3,4-dimethylcyclopent-1-yl-3-methylene, 3,4,4-trimethylcyclopent-1-yl-3-methylene, cyclohex-1-yl-3- or -4-methylene, 3- or 4- or 5-methylcyclohex-1-yl-3- or -4-methylene, 3,4- or 3,5-dimethylcyclohex-1-yl-3- or -4-methylene, 3,4,5- or 3,4,4- or 3,5,5-trimethylcyclohex-1-yl-3- or -4-methylene.

28. A compound according to claim 1, wherein $R_4$ is —$C_yH_{2y}$-cyclohexylene-$C_yH_{2y}$— which is unsubstituted or substituted by 1 to 3 $C_1$–$C_4$alkyl groups.

29. A compound according to claim 28, wherein the —$C_yH_{2y}$— group is methylene.

30. A compound according to claim 28, wherein $R_4$ is cyclohexane-1,3- or -1,4-dimethylene, 3- or 4- or 5-methylcyclohexane-1,3- or -1,4-dimethylene, 3,4- or 3,5-dimethylcyclohexane-1,3- or -1,4-dimethylene or 3,4,5- or 3,4,4- or 3,5,5-trimethylcyclohexane-1,3- or 1,4-dimethylene.

31. A compound according to claim 1, wherein $R_4$ is alkylene which is branched in the α- and β-position to the XCN group, or is a cyclic hydrocarbon substituted by $C_1$–$C_4$ alkyl or $C_1$–$C_4$ alkoxy in at least one α-position.

32. A compound according to claim 1, wherein n in the $R_1$—$(Y_1)_n$— groups is 0, X, Y, $Y_2$ and $Y_1$ in the $R_2$—$(Y_1)_n$— group are each O, n in the $R_2$—$(Y_1)_n$— groups is 0 or 1, $R_1$ is $C_1$–$C_4$ alkyl or phenyl, or the $R_1$—$(Y_1)_n$— groups together are tetramethylene or pentamethylene, $R_2$ is $C_1$–$C_4$ alkyl or H, R is hydrogen, n in the —$(Y_2)_n$— group is 0 or 1, $R_3$ is linear or branched $C_2$–$C_4$ alkylene or a direct bond, in which case n in the —$(Y_2)_n$— group is 0, $R_4$ is branched $C_5$–$C_{10}$ alkylene, phenylene or phenylene which is substituted by 1 to 3 methyl groups, benzylene or benzylene which is substituted by 1 to 3 methyl groups, cyclohexylene or cyclohexylene which is substituted by 1 to 3 methyl groups, cyclohexyl-$C_yH_{2y}$— or —$C_yH_{2y}$-cyclohexyl-$C_yH_{2y}$— or cyclohexyl-$C_yH_{2y}$— or —$C_yH_{2y}$-cyclohexyl-$C_yH_{2y}$—, each of which is substituted by 1 to 3 methyl groups, and y is 1 or 2.

33. A compound according to claim 1, wherein n in the $R_1$—$(Y_1)_n$— and —$(Y_2)_n$— groups is 0, X, Y, $Y_2$ and $Y_1$ in the $R_2$—$(Y_1)_n$— group are each O, n in the $R_2$—$(Y_1)_n$— groups is 0 or 1, $R_1$ is methyl or phenyl, or the $R_1$—$(Y_1)_n$— groups together are tetramethylene or pentamethylene, $R_2$ is methyl or H, R is hydrogen, n in the —$(Y_2)_n$— group is 1, $R_3$ is ethylene, or the n in the —$(Y_2)_n$— group is 0 and $R_3$ is a direct bond, $R_4$ is branched $C_6$–$C_{10}$ alkylene, phenylene or phenylene which is substituted by 1 to 3 methyl groups, benzylene or benzylene which is substituted by 1 to 3 methyl groups, cyclohexylene or cyclohexylene which is substituted by 1 to 3 methyl groups, cyclohexyl-$CH_2$— or cyclohexyl-$CH_2$— which is substituted by 1 to 3 methyl groups.

34. A compound according to claim 1 having a formula selected from the group consisting of:

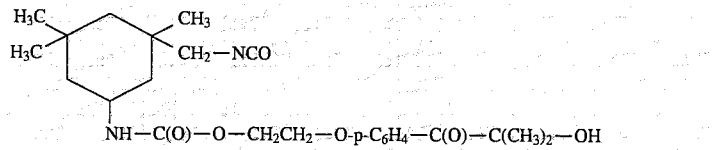

NH—C(O)—O—CH$_2$CH$_2$—O-p-C$_6$H$_4$—C(O)—C(CH$_3$)$_2$—OH

OCNCH$_2$C(CH$_3$)$_2$CH$_2$CH(CH$_3$)(CH$_2$)$_2$NHC(O)O(CH$_2$)$_2$O—⟨phenylene⟩—C(O)C(CH$_3$)$_2$OH;

and

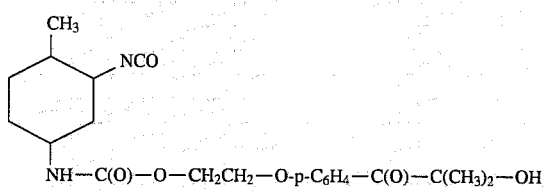

NH—C(O)—O—CH$_2$CH$_2$—O-p-C$_6$H$_4$—C(O)—C(CH$_3$)$_2$—OH

35. A process for the preparation of a compound of formula I of claim 1, which comprises reacting, in an inert solvent, a compound of the formula II:
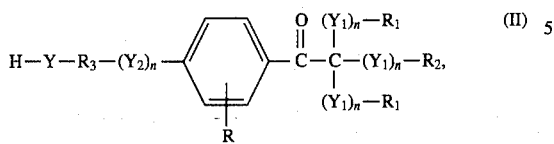
with a diisocyanate of formula III:
$$XCN-R_4-NCX \quad (III),$$
in which Y, $Y_1$, $Y_2$, R, $R_1$, $R_2$, $R_3$, and n are as defined in claim 1, in which $R_4$ and X are as defined in claim 1.
* * * * *